US009445851B2

(12) United States Patent
Walker et al.

(10) Patent No.: US 9,445,851 B2
(45) Date of Patent: Sep. 20, 2016

(54) BONE PLATE SCREW-BLOCKING SYSTEMS AND METHODS

(71) Applicant: Spinal USA, Inc., Parsippany, NJ (US)

(72) Inventors: John Lawrence Walker, Madison, MS (US); James Milton Phillips, Star, MS (US); Jeffrey Johnson, Flowood, MS (US); John Franklin Cummins, Kosciusko, MS (US)

(73) Assignee: Spinal USA, Inc., Parsippany, NJ (US)

( * ) Notice: Subject to any disclaimer, the term of this patent is extended or adjusted under 35 U.S.C. 154(b) by 0 days.

(21) Appl. No.: 14/312,452

(22) Filed: Jun. 23, 2014

(65) Prior Publication Data

US 2014/0371800 A1 Dec. 18, 2014

Related U.S. Application Data

(60) Continuation of application No. 13/802,258, filed on Mar. 13, 2013, now Pat. No. 8,795,341, which is a division of application No. 12/842,901, filed on Jul. 23, 2010, now Pat. No. 8,419,777.

(60) Provisional application No. 61/228,508, filed on Jul. 24, 2009.

(51) Int. Cl.
*A61B 17/80* (2006.01)
*A61B 17/70* (2006.01)

(52) U.S. Cl.
CPC ......... *A61B 17/8061* (2013.01); *A61B 17/808* (2013.01); *A61B 17/8033* (2013.01); *A61B 17/8038* (2013.01); *A61B 17/8042* (2013.01); *A61B 17/7059* (2013.01)

(58) Field of Classification Search
USPC ................................................ 606/295, 289
See application file for complete search history.

(56) References Cited

U.S. PATENT DOCUMENTS 4,488,543 A 12/1984 Tornier
5,006,120 A 4/1991 Carter
(Continued)

FOREIGN PATENT DOCUMENTS

EP 1 346 697 9/2003
JP 2003-265493 9/2003
(Continued)

OTHER PUBLICATIONS

Apr. 14, 2014 Office Action for Japanese Application No. 2012-521843 filed on Jul. 23, 2010.
(Continued)

*Primary Examiner* — Sameh Boles
(74) *Attorney, Agent, or Firm* — Knobbe, Martens, Olson & Bear, LLP.

(57) ABSTRACT

A bone plate screw-blocking system and method that comprises a plate with at least two bone screw receiving holes, blocking elements, bone screws, and a tool capable of simultaneously actuating at least two blocking elements. The plate includes an upper surface and a lower surface with bone screw receiving holes that extend through both surfaces of the plate. The bone screws couple the plate to the bone via the bone screw receiving holes. The blocking elements are movably positioned proximate each bone screw receiving hole. In an initial unblocked position, the blocking elements do not cover the bone screw receiving holes. Upon movement into final blocked positions, the blocking elements cover at least a portion of the bone screw receiving holes and preferably extend over at least a portion of the bone screw during use.

7 Claims, 31 Drawing Sheets

(56) References Cited

U.S. PATENT DOCUMENTS

| | | |
|---|---|---|
| 5,053,036 A | 10/1991 | Perren et al. |
| 5,067,956 A | 11/1991 | Buford, III et al. |
| 5,151,103 A | 9/1992 | Tepic et al. |
| 5,364,399 A | 11/1994 | Lowery et al. |
| 5,487,743 A | 1/1996 | Laurain et al. |
| 5,487,783 A | 1/1996 | Agnello et al. |
| 5,549,612 A | 8/1996 | Yapp et al. |
| 5,578,034 A | 11/1996 | Estes |
| 5,616,144 A | 4/1997 | Yapp et al. |
| 5,662,655 A | 9/1997 | Laboureau et al. |
| 5,931,838 A | 8/1999 | Vito |
| 5,951,558 A | 9/1999 | Fiz |
| 6,139,550 A | 10/2000 | Michelson |
| 6,152,927 A | 11/2000 | Farris et al. |
| 6,171,342 B1 | 1/2001 | O'Neil et al. |
| 6,183,475 B1 | 2/2001 | Lester |
| 6,224,602 B1 | 5/2001 | Hayes |
| 6,235,034 B1 | 5/2001 | Bray |
| 6,258,089 B1 | 7/2001 | Campbell et al. |
| 6,261,291 B1 | 7/2001 | Talaber et al. |
| 6,293,949 B1 | 9/2001 | Justis et al. |
| 6,306,139 B1 | 10/2001 | Fuentes |
| 6,331,179 B1 | 12/2001 | Freid et al. |
| 6,336,928 B1 | 1/2002 | Guerin et al. |
| 6,361,537 B1 | 3/2002 | Anderson |
| 6,398,783 B1 | 6/2002 | Michelson |
| 6,413,259 B1 * | 7/2002 | Lyons et al. .................. 606/295 |
| 6,428,542 B1 | 8/2002 | Michelson |
| 6,454,769 B2 | 9/2002 | Wagner et al. |
| 6,503,250 B2 | 1/2003 | Paul |
| 6,527,776 B1 | 3/2003 | Michelson |
| 6,533,786 B1 | 3/2003 | Needham et al. |
| 6,592,586 B1 | 7/2003 | Michelson |
| 6,599,290 B2 | 7/2003 | Bailey et al. |
| 6,602,255 B1 | 8/2003 | Campbell et al. |
| 6,602,256 B1 | 8/2003 | Hayes |
| 6,626,907 B2 | 9/2003 | Campbell et al. |
| 6,652,525 B1 | 11/2003 | Assaker et al. |
| 6,669,700 B1 | 12/2003 | Farris et al. |
| 6,692,503 B2 | 2/2004 | Foley et al. |
| 6,695,846 B2 | 2/2004 | Richelsoph et al. |
| 6,712,818 B1 | 3/2004 | Michelson |
| 6,755,833 B1 | 6/2004 | Paul et al. |
| 6,761,719 B2 | 7/2004 | Justis et al. |
| 6,793,658 B2 | 9/2004 | LeHuec |
| 6,890,335 B2 | 5/2005 | Grabowski et al. |
| 6,916,320 B2 | 7/2005 | Michelson |
| 6,926,718 B1 | 8/2005 | Michelson |
| 6,936,050 B2 | 8/2005 | Michelson |
| 6,936,051 B2 | 8/2005 | Michelson |
| 6,945,973 B2 | 9/2005 | Bray |
| 6,945,975 B2 | 9/2005 | Dalton |
| 6,969,390 B2 | 11/2005 | Michelson |
| 6,979,334 B2 | 12/2005 | Dalton |
| 6,989,012 B2 | 1/2006 | LeHuec et al. |
| 7,001,387 B2 | 2/2006 | Farris et al. |
| 7,001,389 B1 | 2/2006 | Navarro et al. |
| 7,004,944 B2 | 2/2006 | Gause |
| 7,011,665 B2 | 3/2006 | Null et al. |
| 7,041,105 B2 | 5/2006 | Michelson |
| 7,044,952 B2 | 5/2006 | Michelson |
| 7,048,739 B2 | 5/2006 | Konieczynski et al. |
| 7,060,067 B2 | 6/2006 | Needham et al. |
| 7,074,221 B2 | 7/2006 | Michelson |
| 7,077,844 B2 | 7/2006 | Michelson |
| 7,097,645 B2 | 8/2006 | Michelson |
| 7,118,573 B2 | 10/2006 | Michelson |
| 7,169,150 B2 | 1/2007 | Shipp et al. |
| 7,172,627 B2 | 2/2007 | Fiere et al. |
| 7,210,884 B2 | 5/2007 | Shindoh |
| 7,273,481 B2 | 9/2007 | Lombardo et al. |
| 7,288,094 B2 | 10/2007 | Lindemann et al. |
| 7,288,095 B2 | 10/2007 | Baynham et al. |
| 7,306,605 B2 | 12/2007 | Ross |
| 7,309,340 B2 | 12/2007 | Fallin et al. |
| 7,322,984 B2 | 1/2008 | Doubler et al. |
| 7,438,715 B2 | 10/2008 | Doubler et al. |
| 7,452,370 B2 | 11/2008 | Anderson |
| 7,621,943 B2 | 11/2009 | Michelson |
| 7,625,381 B2 | 12/2009 | Michelson |
| 7,651,497 B2 | 1/2010 | Michelson |
| 7,662,174 B2 | 2/2010 | Doubler et al. |
| 7,674,279 B2 | 3/2010 | Johnson |
| 7,704,250 B2 | 4/2010 | Michelson |
| 7,704,255 B2 | 4/2010 | Michelson |
| 7,740,630 B2 | 6/2010 | Michelson |
| 7,803,157 B2 | 9/2010 | Michelson |
| 7,811,285 B2 | 10/2010 | Michelson |
| 7,824,432 B2 | 11/2010 | Michelson |
| 7,972,366 B2 | 7/2011 | Richelsoph et al. |
| 7,985,224 B2 | 7/2011 | Michelson |
| 8,007,523 B2 | 8/2011 | Wagner et al. |
| 8,043,346 B2 | 10/2011 | Markworth |
| 8,419,777 B2 | 4/2013 | Walker et al. |
| 8,535,354 B2 | 9/2013 | Cummins |
| 8,795,341 B2 | 8/2014 | Walker et al. |
| 2003/0187440 A1 | 10/2003 | Richelsoph et al. |
| 2004/0087951 A1 | 5/2004 | Khalili |
| 2004/0097935 A1 | 5/2004 | Richelsoph et al. |
| 2004/0127900 A1 | 7/2004 | Konieczynski et al. |
| 2004/0153069 A1 | 8/2004 | Paul |
| 2004/0220566 A1 | 11/2004 | Bray |
| 2004/0220571 A1 | 11/2004 | Assaker et al. |
| 2004/0220572 A1 | 11/2004 | Michelson |
| 2004/0236334 A1 | 11/2004 | Michelson |
| 2005/0010226 A1 | 1/2005 | Grady et al. |
| 2005/0010227 A1 | 1/2005 | Paul |
| 2005/0021032 A1 | 1/2005 | Koo |
| 2005/0033294 A1 | 2/2005 | Garden et al. |
| 2005/0075633 A1 | 4/2005 | Ross |
| 2005/0131412 A1 | 6/2005 | Olevsky et al. |
| 2005/0187551 A1 | 8/2005 | Orbay et al. |
| 2005/0187553 A1 | 8/2005 | Grabowski et al. |
| 2005/0228386 A1 | 10/2005 | Ziolo et al. |
| 2005/0251138 A1 | 11/2005 | Boris et al. |
| 2005/0261390 A1 | 11/2005 | Frances et al. |
| 2005/0261689 A1 | 11/2005 | Lin |
| 2005/0277933 A1 | 12/2005 | Wall et al. |
| 2005/0283152 A1 | 12/2005 | Lindemann et al. |
| 2006/0009770 A1 | 1/2006 | Speirs et al. |
| 2006/0064097 A1 | 3/2006 | Bray |
| 2006/0085001 A1 | 4/2006 | Michelson |
| 2006/0100626 A1 | 5/2006 | Rathbun et al. |
| 2006/0106387 A1 * | 5/2006 | Fanger ............... A61B 17/7059 606/281 |
| 2006/0122603 A1 | 6/2006 | Kolb |
| 2006/0122604 A1 | 6/2006 | Gorhan et al. |
| 2006/0122605 A1 | 6/2006 | Suh et al. |
| 2006/0149241 A1 | 7/2006 | Richelsoph et al. |
| 2006/0149256 A1 | 7/2006 | Wagner et al. |
| 2006/0155285 A1 | 7/2006 | Anderson |
| 2006/0161157 A1 | 7/2006 | Mosca et al. |
| 2006/0189997 A1 | 8/2006 | Guenther et al. |
| 2006/0276793 A1 | 12/2006 | Berry |
| 2006/0293668 A1 | 12/2006 | May et al. |
| 2007/0043366 A1 | 2/2007 | Pfefferle et al. |
| 2007/0073297 A1 | 3/2007 | Reynolds |
| 2007/0123879 A1 | 5/2007 | Songer et al. |
| 2007/0123884 A1 | 5/2007 | Abdou |
| 2007/0162013 A1 | 7/2007 | Jacene et al. |
| 2007/0162019 A1 | 7/2007 | Burns et al. |
| 2007/0213728 A1 * | 9/2007 | Lindemann ........ A61B 17/8042 606/279 |
| 2007/0225718 A1 | 9/2007 | Ensign |
| 2007/0239163 A1 | 10/2007 | Strnad et al. |
| 2008/0009870 A1 | 1/2008 | Lombardo et al. |
| 2008/0015592 A1 | 1/2008 | Long et al. |
| 2008/0021477 A1 | 1/2008 | Strnad et al. |
| 2008/0033437 A1 | 2/2008 | Shipp et al. |
| 2008/0091206 A1 | 4/2008 | Johnson |
| 2008/0097443 A1 | 4/2008 | Campbell |
| 2008/0097444 A1 | 4/2008 | Erickson et al. |
| 2008/0114359 A1 | 5/2008 | Murner et al. |
| 2008/0161862 A1 | 7/2008 | Ensign |

(56) References Cited

U.S. PATENT DOCUMENTS

| | | |
|---|---|---|
| 2008/0172092 A1 | 7/2008 | Kraemer |
| 2008/0177330 A1 | 7/2008 | Ralph et al. |
| 2008/0234748 A1 | 9/2008 | Wallenstein et al. |
| 2008/0243192 A1 | 10/2008 | Jacene et al. |
| 2008/0269807 A1 | 10/2008 | Simon et al. |
| 2008/0287999 A1 | 11/2008 | Markworth |
| 2009/0062863 A1 | 3/2009 | Peppers |
| 2011/0022096 A1 | 1/2011 | Cummins et al. |
| 2011/0022097 A1 | 1/2011 | Walker et al. |
| 2014/0228892 A1 | 8/2014 | Cummins |

FOREIGN PATENT DOCUMENTS

| | | |
|---|---|---|
| JP | 2008-86817 | 4/2008 |
| WO | WO 98/34556 | 8/1998 |
| WO | WO 2004/039236 | 5/2004 |
| WO | WO 2006/101837 | 9/2006 |
| WO | WO 2009/061517 A1 | 5/2009 |

OTHER PUBLICATIONS

U.S. Appl. No. 12/842,901, filed Jul. 23, 2010, Walker et al.
U.S. Appl. No. 12/842,517, filed Jul. 23, 2010, Cummins et al.
International Search Report and Written Opinion for co-pending International Application No. PCT/US2010/043116 mailed Feb. 28, 2011 in 12 pages.
International Preliminary Report on Patentability for related PCT Application No. PCT/US2010/043116, issued on Jan. 24, 2012, in 5 pages.
International Search Report and Written Opinion for co-pending International Application No. PCT/US2010/043106 mailed Feb. 28, 2011 in 13 pages.
International Preliminary Report on Patentability for related PCT Application No. PCT/US2010/043106, issued on Jan. 24, 2012, in 5 pages.
Supplementary Search Report and Written Opinion prepare by European Patent Office on Nov. 21, 2013 in the corresponding European patent application No. EP 10802977.8—8 pages.

\* cited by examiner

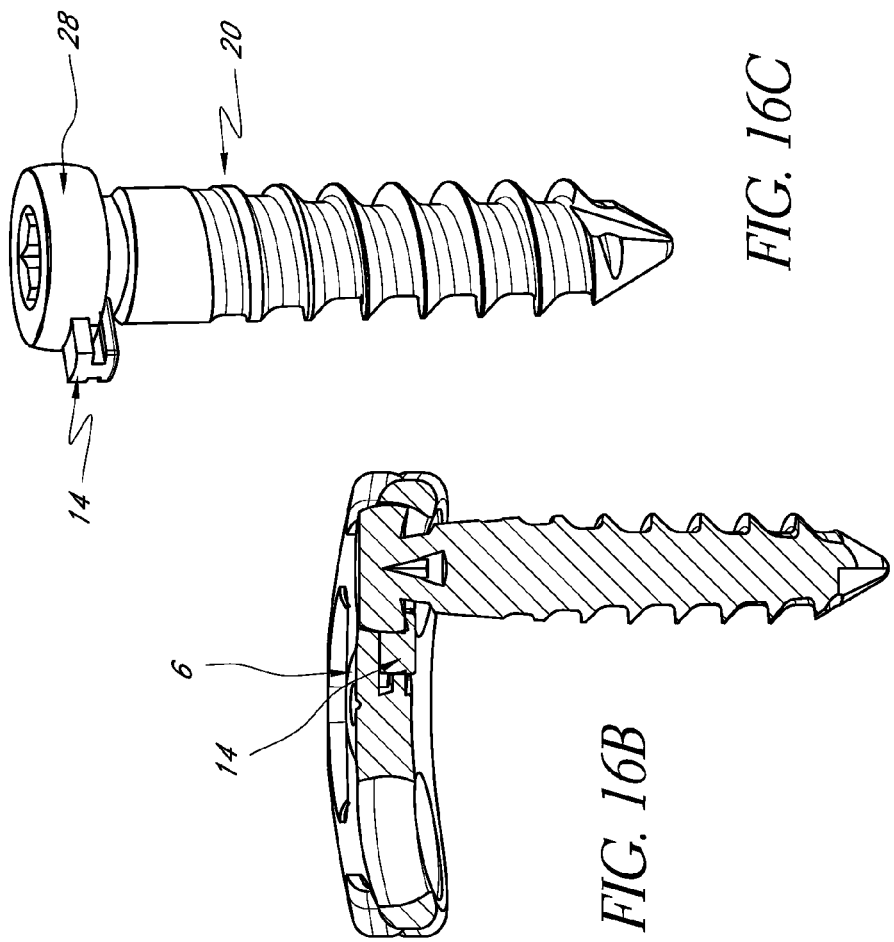
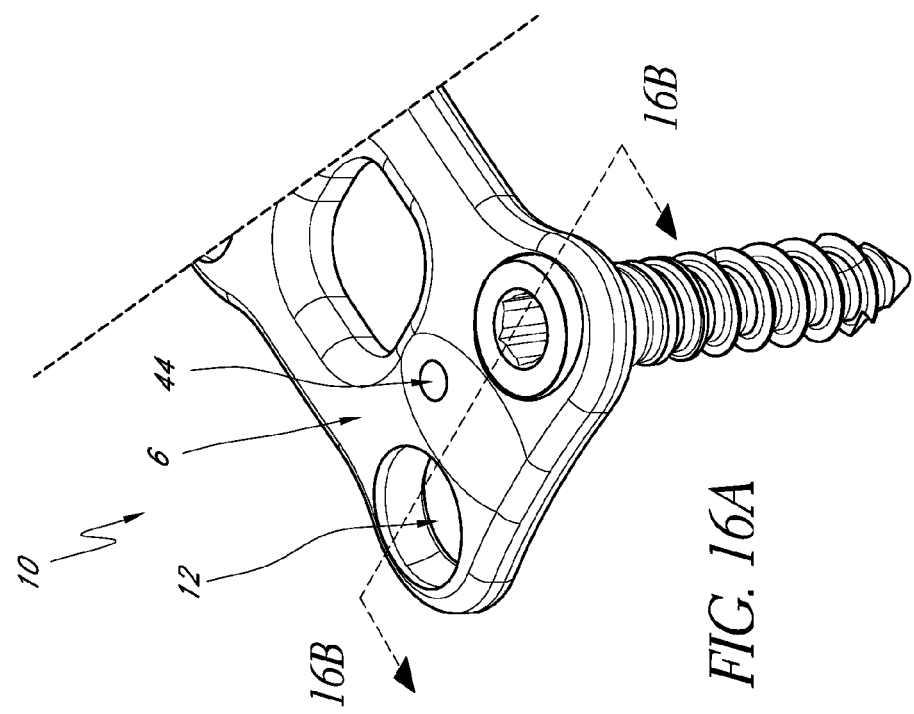
FIG. 16C
FIG. 16B
FIG. 16A

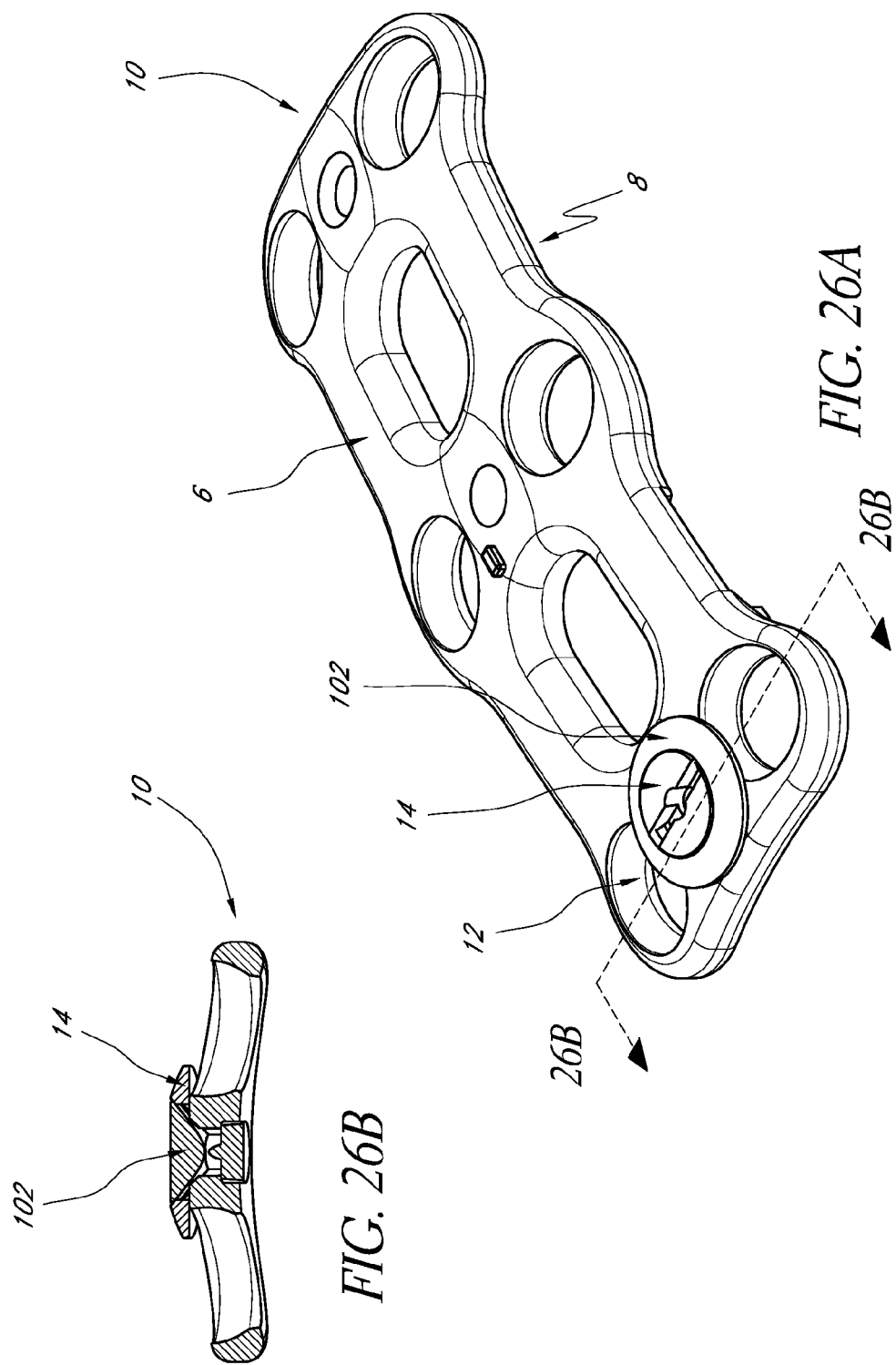

BONE PLATE SCREW-BLOCKING SYSTEMS AND METHODS

CROSS-REFERENCE TO RELATED APPLICATIONS

Any and all applications for which a foreign or domestic priority claim is identified in the Application Data Sheet as filed with the present application, are hereby incorporated by reference in their entirety under 37 CFR 1.57. This application is a continuation of U.S. patent application Ser. No. 13/802,258 entitled "BONE PLATE SCREW-BLOCKING SYSTEMS AND METHODS", filed Mar. 13, 2013, which is a divisional of U.S. patent application Ser. No. 12/842,901, now U.S. Pat. No. 8,419,777, entitled "BONE PLATE SCREW-BLOCKING SYSTEMS AND METHODS", filed Jul. 23, 2010, which claims the priority benefit of U.S. Provisional Application Ser. No. 61/228,508, filed on Jul. 24, 2009, the entirety of which are hereby incorporated by reference.

BACKGROUND OF THE INVENTION

1. Field of the Invention

Disclosed herein are bone plating systems and methods related to the field of orthopedic surgery. More particularly, certain embodiments disclosed herein relate to bone plate systems and methods with a screw-blocking element used in lumbar, cervical, and thoracic spinal regions.

2. Description of the Related Art

Spinal fusion encompasses a surgical technique in which two or more vertebrae are connected together. This technique may be used for multiple indications, including abnormal spinal curvature (e.g., scoliosis) and weakening or injuring of the vertebrae or spinal disc.

In some instances, this process is accomplished and/or supplemented using a plate to join together adjacent vertebrae. The plate is affixed by implanting a plurality of screws through the plate and into the vertebrae bodies of adjacent vertebrae. A screw may have an enlarged head that interfaces with the plate having a corresponding cavity, thus allowing for a range of polyaxial articulation between the screw and the plate. A common risk with prior bone plate system designs include backing out and loosening of the screw after being implanted.

SUMMARY OF THE INVENTION

Described herein are bone plate screw-blocking systems that may include a plate, blocking elements, bone screws, and a tool. Methods of assembling and implanting bone plate screw-blocking systems are also included. These bone plate screw-blocking systems are described in greater detail below.

According to one embodiment, a bone plating system comprises a plate having an upper surface, a lower surface and a plurality of bone screw receiving holes defined in the plate and extending between the upper surface and the lower surface. The system comprises a plurality of bone screws having shaft portions and head portions, the head portions being receivable within the plurality of bone screw receiving holes. A plurality of blocking elements are coupled to the plate proximate the bone screw receiving holes. According to some embodiments, the blocking elements are moveable between a first unblocked position and a second blocked position. In some embodiments, a tool comprises an actuation portion and is configured to be positioned between the first and second blocking elements. Rotation of the actuation portion causes blocking elements to simultaneously rotate from the first unblocked position to the second blocked position.

According to another embodiment, a bone plate screw-blocking system includes a plate with at least two bone screw receiving holes, blocking elements, bone screws, and a tool capable of moving at least one blocking element. The plate includes an upper surface and a lower surface with bone screw receiving holes that extend through both surfaces of the plate. The bone screws attach the plate to the bone via the bone screw receiving holes. The blocking elements are rotatably positioned proximate each bone screw receiving hole. In an initial unblocked position, the blocking elements do not cover the bone screw receiving holes. According to one embodiment, upon rotation into final blocked positions, the blocking elements preferably cover, at least in part, the bone screw receiving holes, yet do not contact the bone screw.

According to another embodiment, the bone plate screw-blocking system preferably includes a plate with an upper surface, lower surface, and at least first and second bone screw receiving holes. The bone screw receiving holes extend between the upper surface and the lower surface of the plate. The bone screw receiving holes are preferably defined by a partially cylindrical bone-screw-shaft-receiving portion and a second partially spherical bone-screw-head-seating portion. The system comprises at least first and second bone screws each containing a shaft portion and head portion. The shaft portions are configured to be anchored in bone and receivable within the bone-screw-shaft-receiving portion. The head portions are receivable with the bone-screw-head-seating portions. The system comprises at least first and second blocking elements coupled to the plate proximate the first and second bone screw receiving holes respectively. The blocking elements preferably comprise non-circular washers riveted to the plate, the washers positioned above the upper surface of the plate. The blocking elements preferably comprise a first blocking edge generally facing toward the bone screw receiving hole and second tool contacting edge generally facing away from the bone screw receiving hole. The blocking elements are rotatable from a first unblocked position to a second blocked position where the blocking elements extend over at least a portion of the corresponding bone screw receiving hole. Upon rotation, the blocking elements preferably do not contact the head of the bone screw, but are configured to limit backout of the bone screw beyond the upper surface of the plate. The system preferably comprises a tool with an actuation portion having a perimeter surface and a first cross-sectional length dimension greater than a second cross-sectional width dimension. The actuation portion of the tool is positioned proximate the plate between the first and second blocking elements when the blocking elements are in the first unblocked position. The width dimension of the actuation portion preferably is less than or equal to the distance between the tool contacting edges of the first and second blocking elements in the first unblocked position. Upon rotation of the tool, the perimeter surface of the actuation portion of the tool contacts the tool contacting surfaces of the blocking elements to simultaneously rotate the blocking elements to at least partially cover the corresponding bone screw receiving holes. The rotation of the blocking elements toward the corresponding bone screw receiving holes is achieved by rotating the greater cross-sectional length dimension in the space between tool contacting surfaces of the first and second blocking elements.

According to one application, a method of using a bone plating system comprises providing a plate having a plurality of bone screw receiving holes, a plurality of blocking elements coupled with the plate proximate the bone screw receiving holes, a plurality of bone screws, and a tool. The plate is positioned proximate the spine during spinal surgery. The bone screws are positioned within the bone screw receiving holes. The tool is positioned proximate the plate between at least two of the plurality of blocking elements. The tool is simultaneously actuated causing the at least two blocking elements to move from a first unblocked position to a second blocked position such that the at least two blocking elements block the bone screws from completely backing out of the plate.

According to another embodiment, a plate comprises an upper surface, a lower surface, and a plurality of bone screw receiving holes defined in the plate and extending between the upper surface and the lower surface. A plurality of bone screws comprises shaft portions and head portions, the head portions being receivable within the plurality of bone screw receiving holes. A plurality of blocking elements are coupled to the plate proximate the bone screw receiving holes, the blocking elements being moveable from a first unblocked position to a second blocked position. In some embodiments, the blocking elements are slidable between a first unblocked position and a second blocked position. In some embodiments, the blocking elements are depressible between a first unblocked position and a second blocked position. In some embodiments, the blocking elements are adjustable between a first unblocked position and a second blocked position.

According to another embodiment, the blocking elements are ring-shaped and mounted onto the plate surrounding a central set screw. The blocking elements may be fixed from an adjustable first unblocked position to a second blocked position by tightening the central set screw into the plate. In yet another embodiment, the blocking elements contain a cutout that limits contact with the bone screw in an initial unblocked position. The blocking elements may be rotated to contact the side of the enlarged head of the bone screw.

In some embodiments, each blocking element corresponds with and blocks exactly one bone screw. However, in other embodiments, each blocking element corresponds with and blocks at least two bone screws. The entire plating system may contain exactly three bone screws and three blocking elements.

In some embodiments, a blocking element is offset from the corresponding bone screw receiving holes in an initial unblocked position. A blocking element may have an attached stud to mate with a groove in the plate to create a more controlled and tracked movement of the blocking element.

In other embodiments, a blocking element is adapted to engage with the side of at least one bone screw. In yet another embodiment, the plate contains a stopper that limits the rotation of at least one corresponding blocking element in a second blocked position.

In another embodiment, a bone plating system comprises a plate comprising an upper surface, a lower surface and a plurality of bone screw receiving holes defined in the plate and extending between the upper surface and the lower surface. A plurality of blocking elements are coupled to the plate proximate the bone screw receiving holes. The blocking elements are adapted to be simultaneously rotatable between a first unblocked position and a second blocked position.

In another embodiment, a bone plating tool for use with a bone plating system comprises a handle portion. An actuation portion is configured to be positioned between first and second blocking elements of a bone plate having a plurality of bone screw receiving holes such that actuation of the actuation portion causes blocking elements to simultaneously rotate first and second blocking elements from a first unblocked position to a second blocked position relative to corresponding bone screw receiving holes.

According to another aspect, a method of using a bone plating system includes providing a plate having a plurality of bone screw receiving holes, a plurality of blocking elements coupled with the plate proximate the bone screw receiving holes, and a plurality of bone screws. The method further includes positioning the plate proximate the spine during spinal surgery, positioning the bone screws within the bone screw receiving holes, and causing the at least two blocking elements to move from a first unblocked position to a second blocked position such that the at least two blocking elements block the bone screws from completely backing out of the plate. In some embodiments, the blocking elements are slidable between a first unblocked position and a second blocked position. In some embodiments, the blocking elements are depressible between a first unblocked position and a second blocked position. In some embodiments, the blocking elements are adjustable between a first unblocked position and a second blocked position. In some embodiments, the blocking elements are rotatable between a first unblocked position and a second blocked position. In some embodiments, a tool can be used to actuate one or more blocking elements between a first unblocked position and a second blocked position.

BRIEF DESCRIPTION OF THE DRAWINGS

FIG. 16A is a proximal perspective view of plate and a bone screw of a bone plate system.

FIG. 16B is a cross-sectional view of the plate illustrated in FIG. 16A.

FIG. 16C is a side perspective view of a screw and blocking element of the plate illustrated in FIG. 16A.

FIG. 26A is a perspective view of one embodiment of a blocking element, central set screw, and a plate of a bone plate system.

FIG. 26B is a cross-sectional view of the plate illustrated in FIG. 25A.

DETAILED DESCRIPTION OF THE PREFERRED EMBODIMENT

Figure 1:
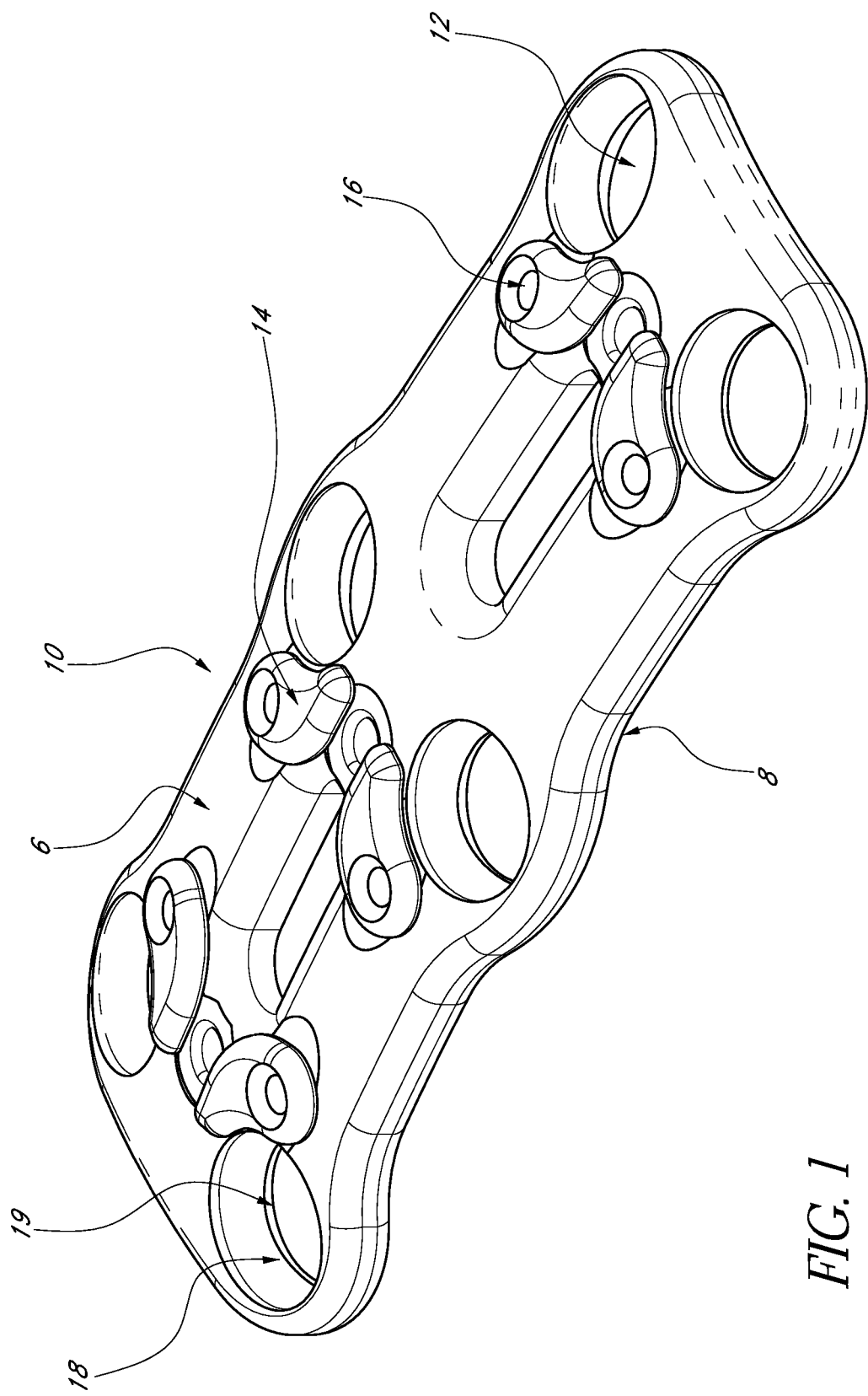
FIG. 1 is a perspective view of one embodiment for a plate and blocking elements of a bone plate system.

Described herein are bone plate screw-blocking systems that may include a plate, blocking elements, bone screws, and a tool. Methods of assembling and implanting bone plate screw-blocking systems are also included. According to some embodiments, blocking elements 14 may be rotatable, slidable, adjustable, and/or depressible from a first unblocked position to a second blocked position. Embodiments may use a variety of methods to hold blocking elements 14 in a second blocked position including a surface frictional force, a set screw, a stopper, a stud, or engagement with a bone screw 20. Blocking elements 14 may be attached to plate 10 via various mechanisms including set screws, rivets, recesses, and lip projections. Blocking elements 14 may be mounted on plate 10 before or after the insertion of bone screws 20.

In certain embodiments, blocking elements 14 are designed to block one corresponding bone screw receiving hole 12. In other embodiments, blocking elements 14 are designed to block more that one corresponding bone screw receiving holes 12. Some of the following embodiments are described to contain blocking elements 14 that block exactly one corresponding bone screw receiving hole 12, however, in some alternative configurations, these blocking elements, or modifications thereof, could be arranged to block multiple screw receiving holes. Similarly, some of the following embodiments are described to contain blocking elements 14 that simultaneously block multiple corresponding bone screw receiving holes 12, however, in some alternative configurations, these blocking elements, or modifications thereof, could be arranged to only block a single screw receiving hole. Accordingly, while some preferred embodiments are disclosed, alternative arrangements and configurations are contemplated and within the scope of the present application.

Figure 2:
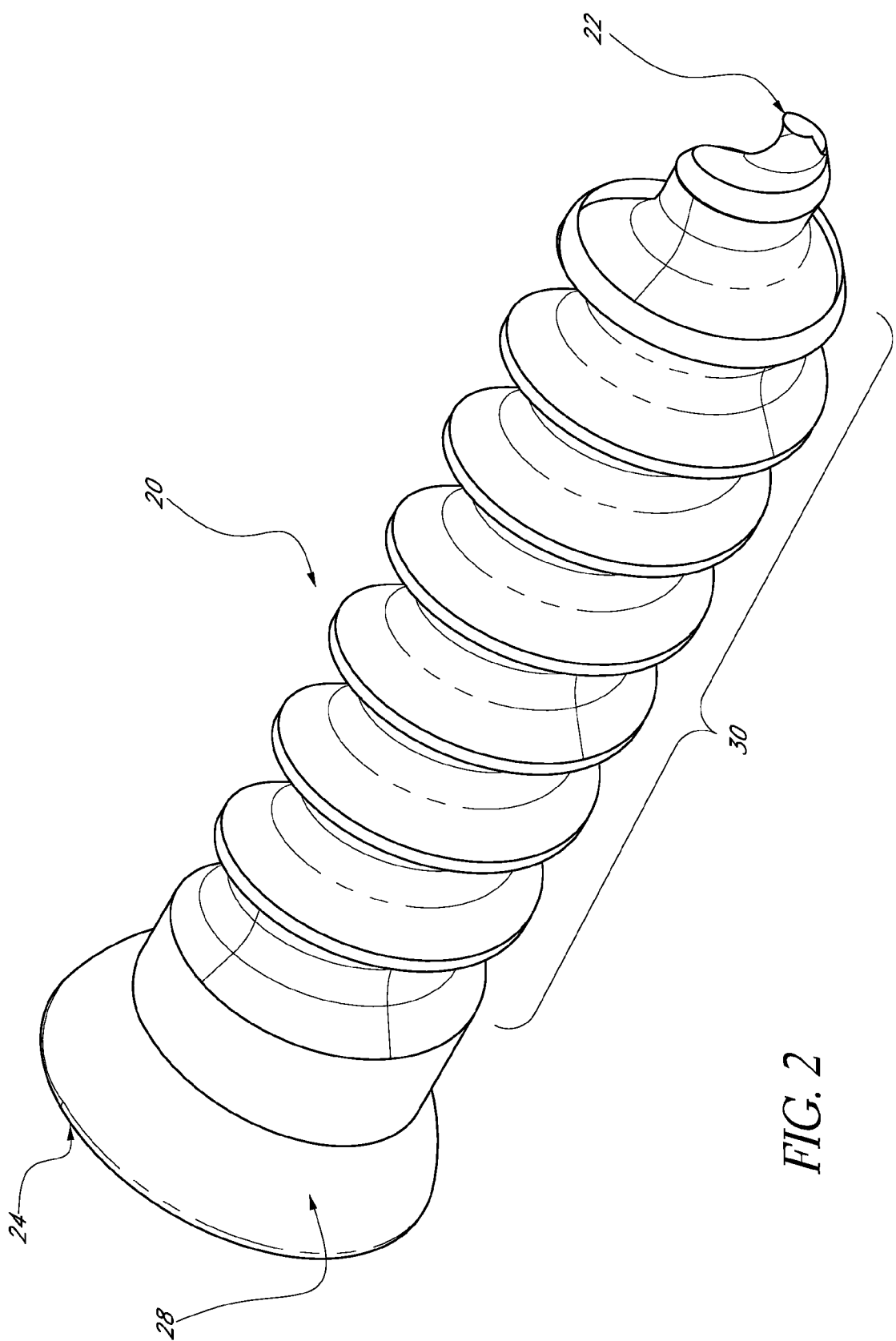
FIG. 2 is a perspective view of one embodiment of a screw for a bone plate system.
Figure 9:
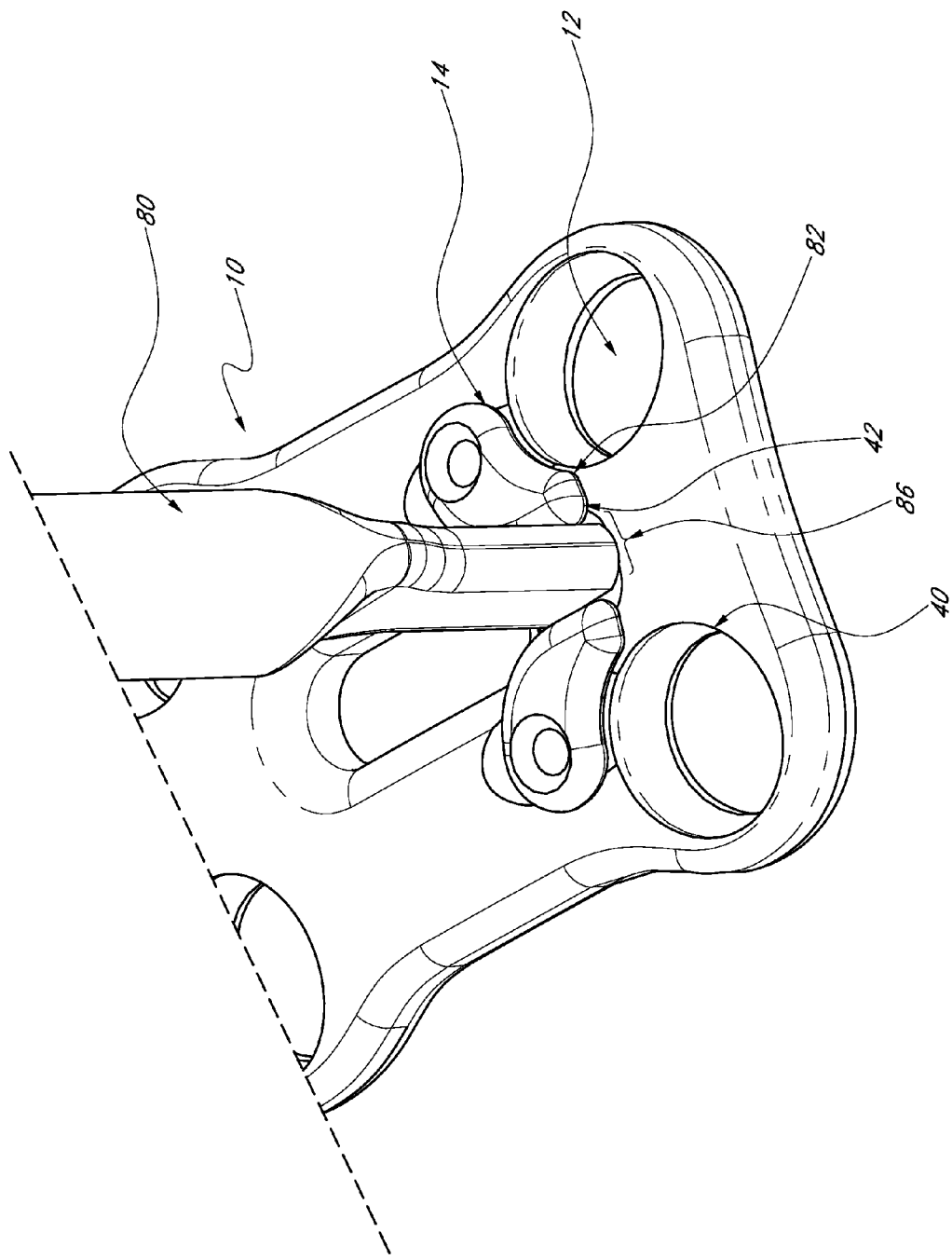
FIG. 9 is a schematic view of a plate, blocking elements, and a tool wherein the blocking elements are in an unlocked position and the tool is in an initial position.
Figure 10:
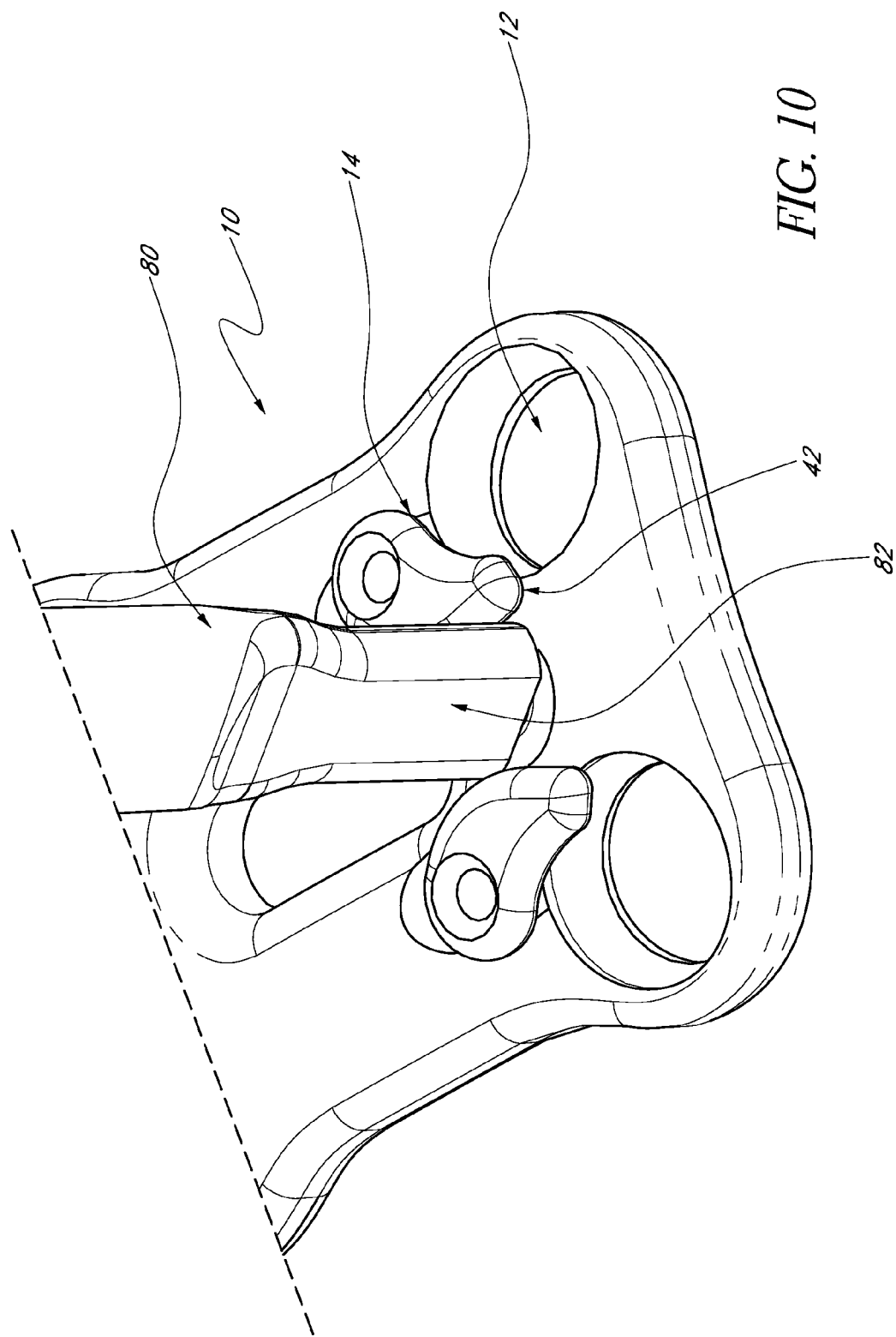
FIG. 10 is a schematic view of a plate, blocking elements, and a tool wherein the blocking elements are rotated due to initial rotation of the tool from an initial position to an intermediate position.
Figure 11:
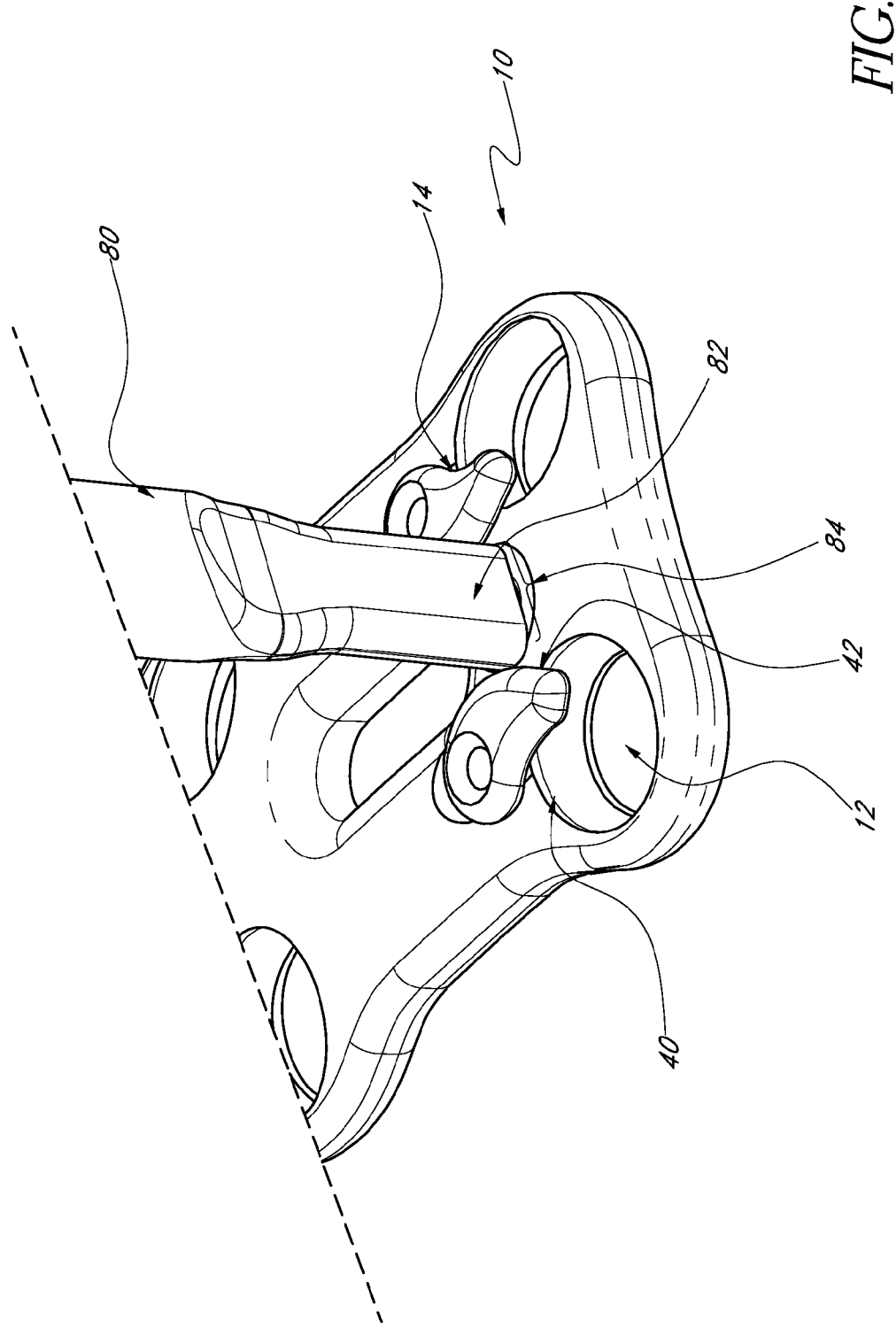
FIG. 11 is a schematic view of a plate, blocking elements, and a tool wherein the blocking elements are in a locked position and the tool has been rotated from an initial position to a final position.
Figure 12:
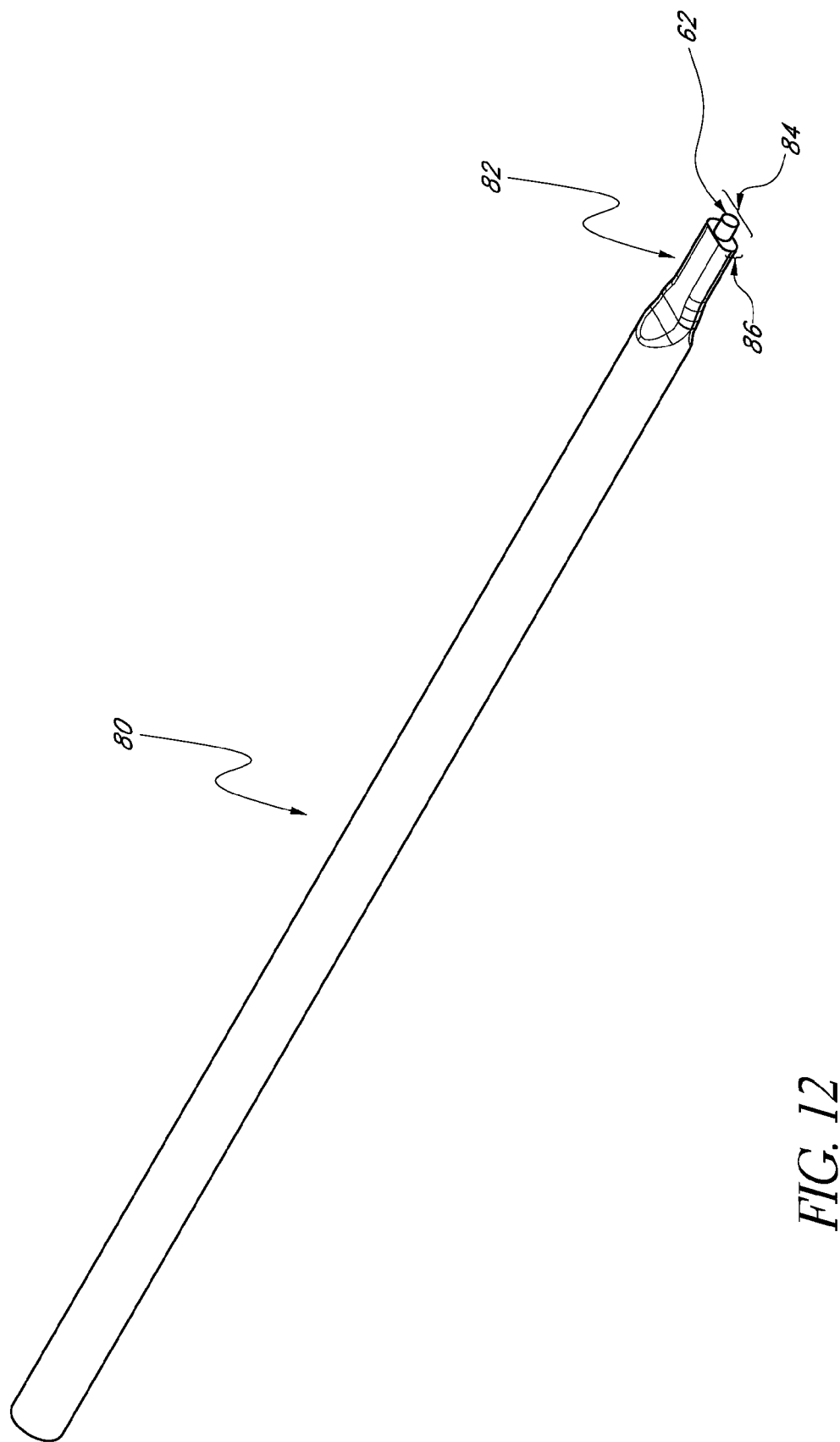
FIG. 12 is a perspective view of one embodiment of a tool.

According to one embodiment, a bone plate screw-blocking system comprises a plate 10, two or more bone screw receiving holes 12, two or more blocking elements 14, and a tool 80, as shown, for example, in FIGS. 1, 2 and 12. As illustrated in FIG. 1, plate 10 includes an upper surface 6 and a lower surface 8. FIG. 2 illustrates one embodiment of bone screw 20. In certain embodiments, bone screw 20 is inserted into plate 10 and screwed into the vertebra. In certain embodiments, blocking element 14 can be rotated between an unblocked position and a blocked position so that in a blocked position, bone screw 20 will resist backing out of plate 10. FIGS. 9-11 illustrate one embodiment of a bone plate locking system in which a tool 80 is used to simultaneously rotate blocking elements 14 from initial unblocked positions (as seen in FIG. 9) to final blocked positions (as seen in FIG. 11).

FIG. 2 illustrates a distal view of one embodiment of a bone screw 20. The bone screw 20 may be a threaded screw body with a shaft portion 30 and head portion 28. The bone screw 20 may have a proximal end 24 and a distal end 22. The distal end 22 may be at least partially threaded. In some embodiments, the distal end 22 of the bone screw 20 may be adapted for implantation into the spine of a patient. For example, the distal end 22 of the bone screw 20 can be adapted for implantation into a vertebral body of a patient's lumbar, cervical, or thoracic spine. The proximal end 24 may include an enlarged head 28.

Figure 3:
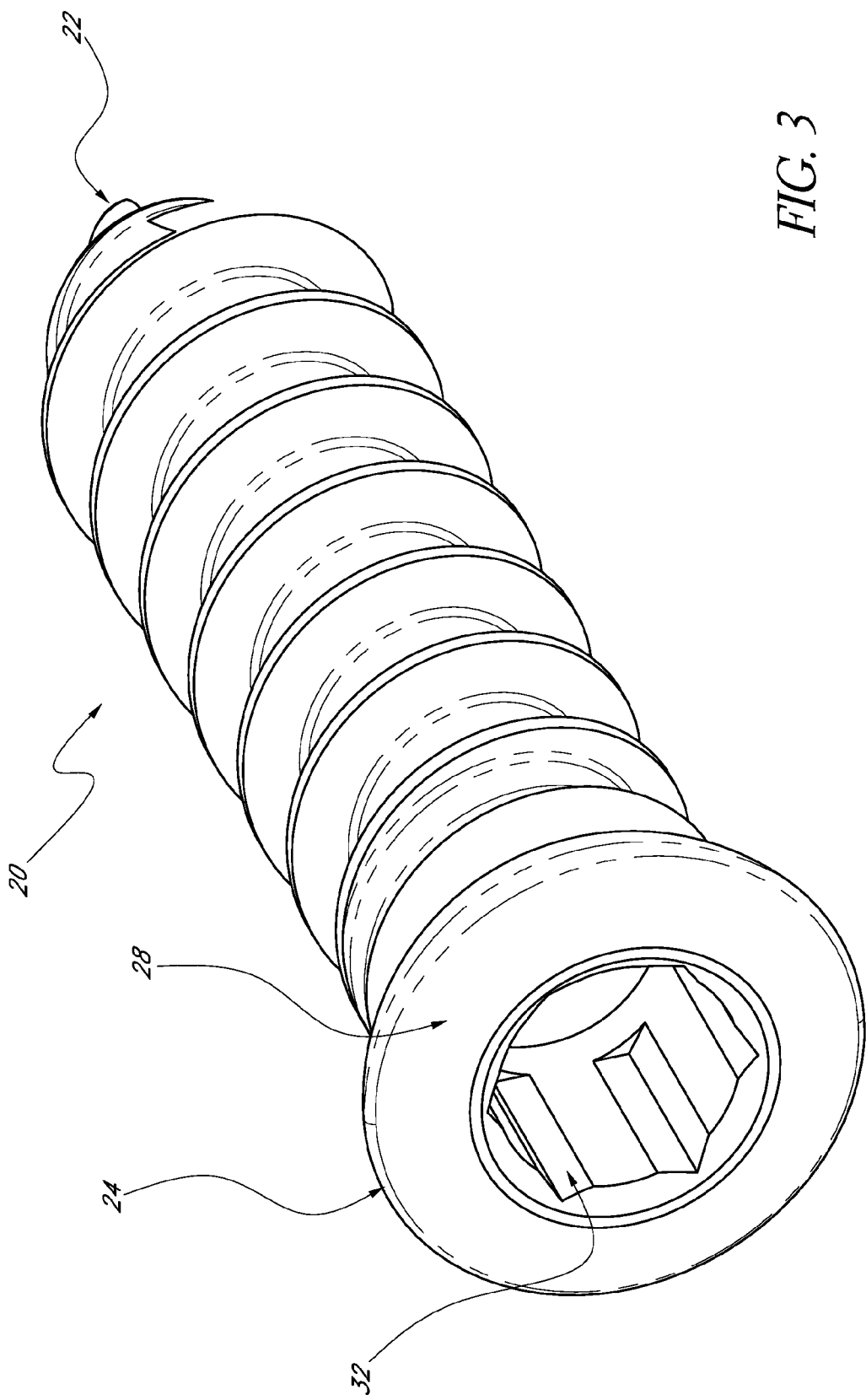
FIG. 3 is a proximal perspective view of the screw illustrated in FIG. 2.
Figure 4:
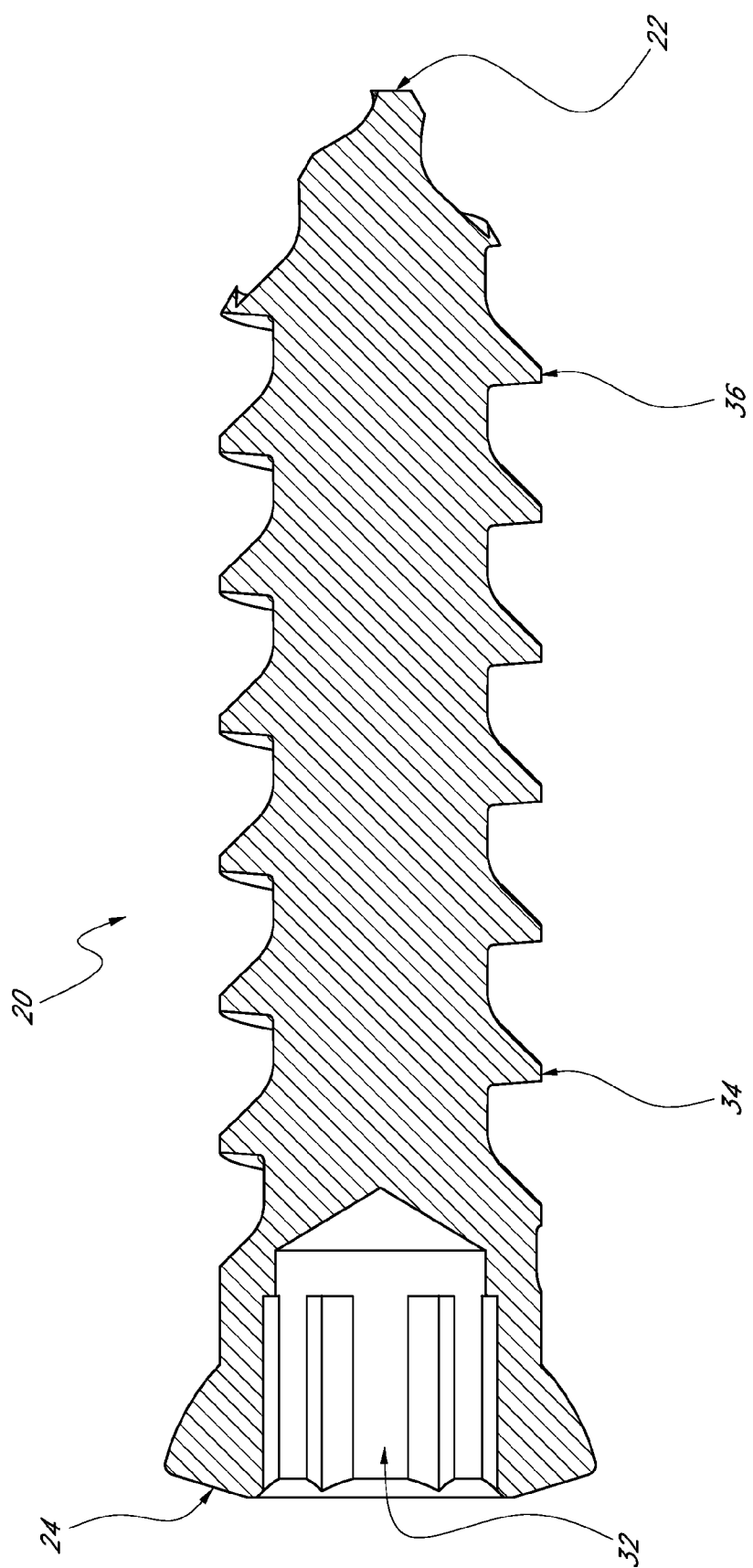
FIG. 4 is a cross-sectional view of the screw illustrated in FIG. 2.

FIG. 3 illustrates a proximal view of the bone screw 20. The enlarged head 28 may include a hexagonal cutout 32 used to rotate the bone screw 20 into the vertebra of the patient. FIG. 4 illustrates a cross-sectional view of bone screw 20. The bone screw 20 may include proximal threading 34 with a constant diameter throughout the shaft of the bone screw 20, ending with the distal threading 36 that precedes a narrower distal end 22. The enlarged head 28 of bone screw 20 may be configured to be recessed below the upper surface 6 of the plate 10.

FIG. 1 illustrates one embodiment of plate 10 with bone screw receiving holes 12 that contain bone-screw-head-seating portion 18 configured to receive the head 28 of bone screw 20 and a bone-screw-shaft receiving portion 19 configured to receive the shaft portion 30 of the bone screw 20. In certain embodiments, the bone screw receiving holes 12 may be entirely cylindrical while in other embodiments the bone-screw-head-seating portion 18 may be curved or angled and the bone-screw-shaft receiving portion 19 may be cylindrical. For example, the bone-screw-head-seating portion 18 may include a spherical, semi-spherical, ball-shaped, cupping-shaped, conical, faceted, grooved, or other curved or angled seating surface to seat the head of the screw. In some embodiments, the bone-screw-shaft receiving portion 19 may also have curved or angled surfaces, or may be combined with the bone-screw-head-seating portion 18.

Figure 5:
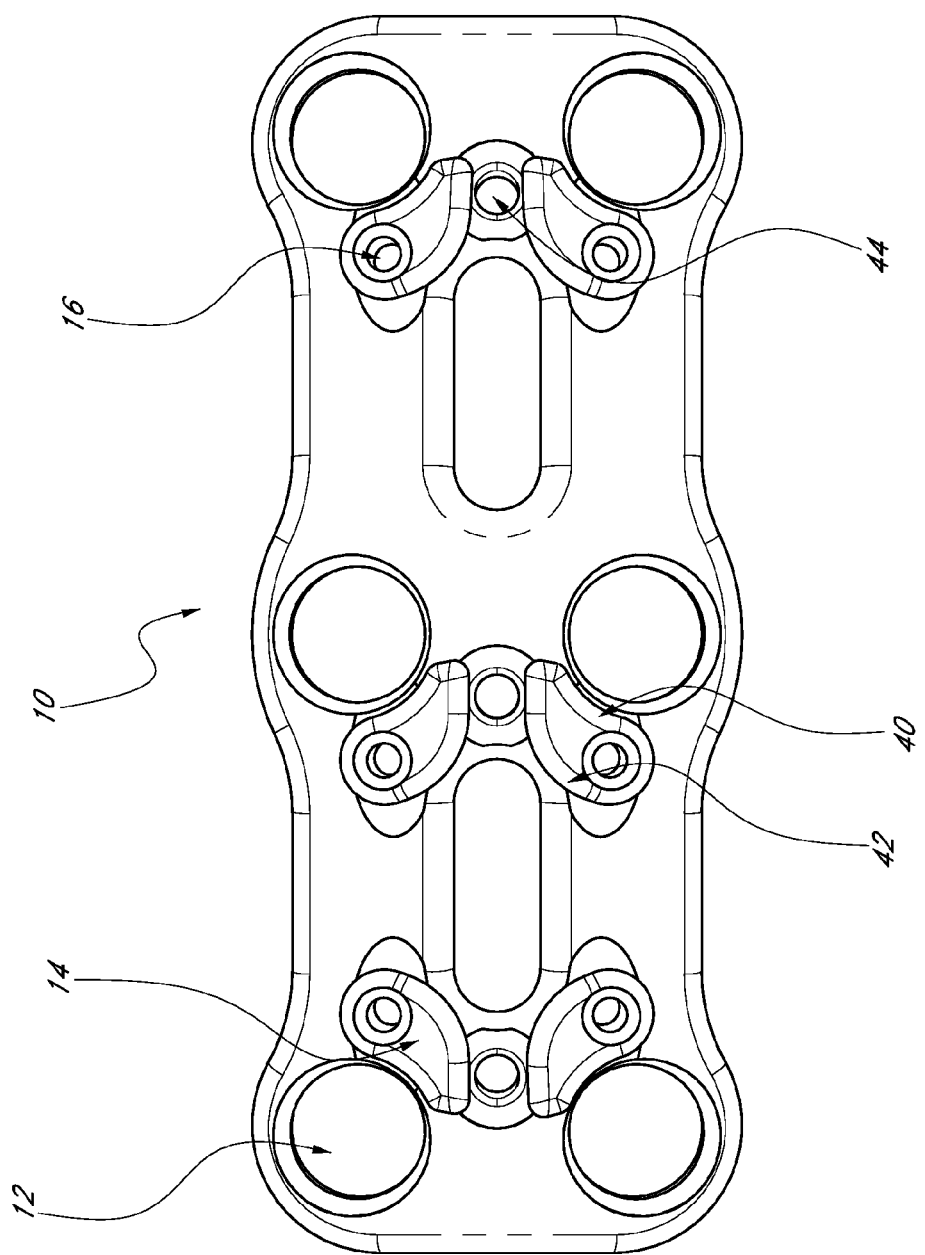
FIG. 5 is a top view of the plate illustrated in FIG. 1.

FIG. 5 illustrates a top view of the plate 10. In some embodiments, one blocking element 14 can be configured to correspond to exactly one bone screw receiving hole 12. In certain embodiments, blocking element 14 may be coupled to the plate via a rivet 16. In other embodiments, blocking element 14 may be coupled to the plate via various mechanisms including but not limited to a set screw, push pin, ring, or recessed groove. The rivet 16 allows for blocking element 14 to be rotated to at least partially cover bone screw receiving hole 12. In one embodiment, blocking element 14 may be a non-circular washer defined by a first blocking surface 40 generally facing toward bone screw receiving hole 12 and a second tool contacting surface 42 generally facing away from the bone screw receiving hole 12.

Figure 6:
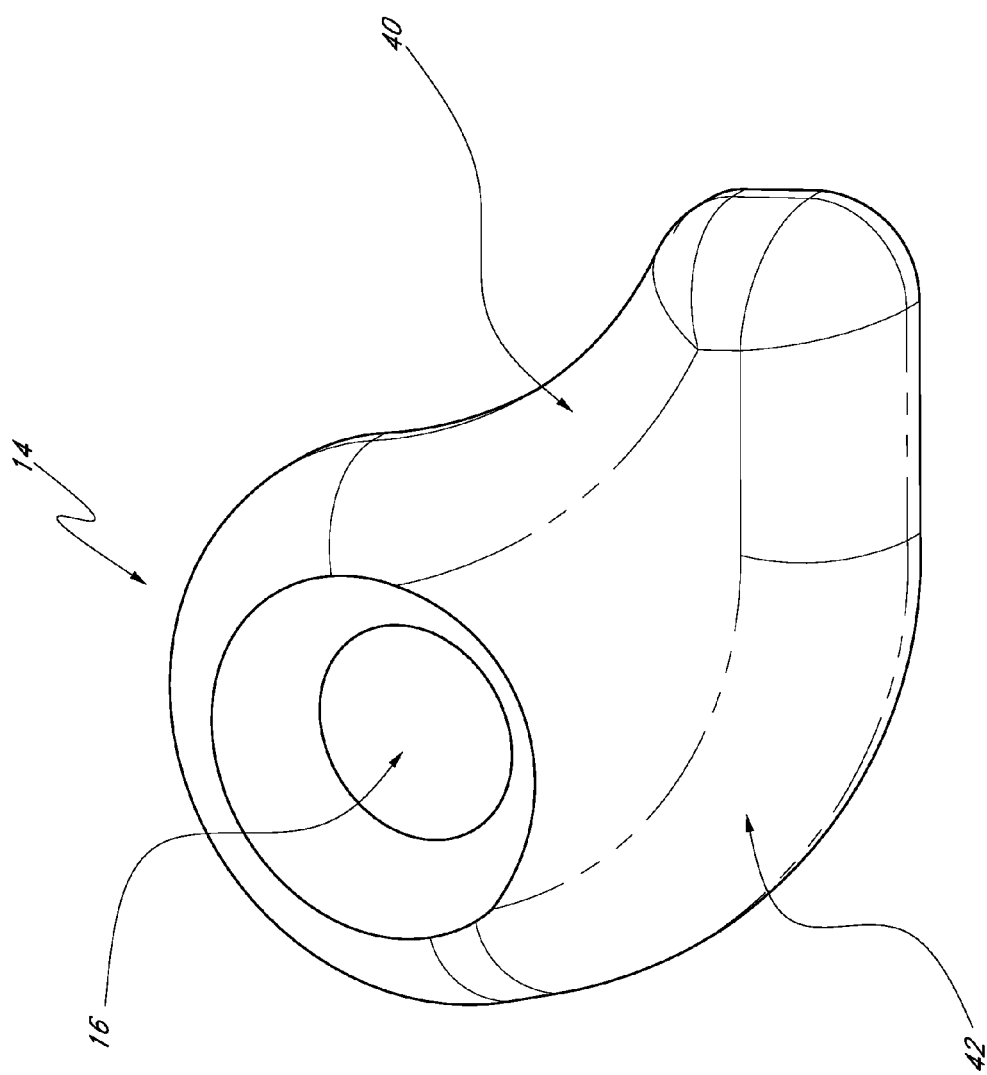
FIG. 6 is a top perspective view of the blocking element illustrated in FIG. 1.
Figure 7:
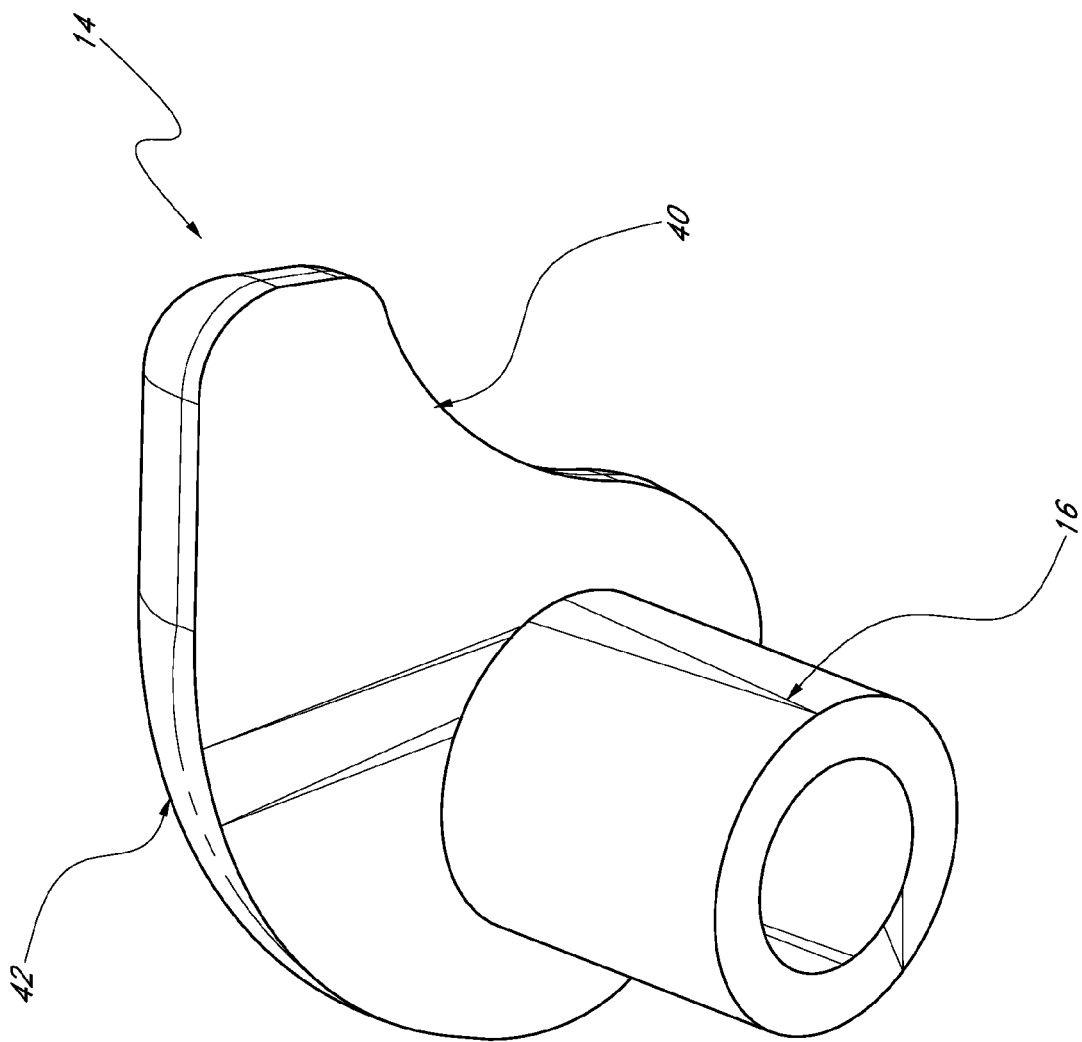
FIG. 7 is a bottom perspective view of the blocking element illustrated in FIG. 6.

FIGS. 6 and 7 illustrate top and bottom views of one embodiment of blocking element 14 respectively. FIG. 6 illustrates the top view with tool contacting surface 42 which can be used to rotate blocking element 14 by use of tool 80, as shown for example in FIG. 12, into blocked position to at least partially cover bone screw receiving hole 12. In other embodiments, blocking element 14 may be rotated through other means or by contacting other portions of blocking element 14 in order to rotate it into blocked position to at least partially cover bone screw receiving hole 12. FIG. 7 illustrates a bottom view of blocking element 14, rivet 16, blocking surface 40, and tool contacting surface 42. In certain embodiments, blocking surface 40 may be curved to generally correspond to a curved profile of a bone screw receiving hole 12. Tool contacting surface 42 may also be curved to provide a more space efficient blocking element 14. For example, in yet other embodiments, one or more of surfaces 40 and 42 of blocking element may be straight, angled, curved, or otherwise shaped to facilitate placement and actuation of blocking elements on the plate.

Figure 8:
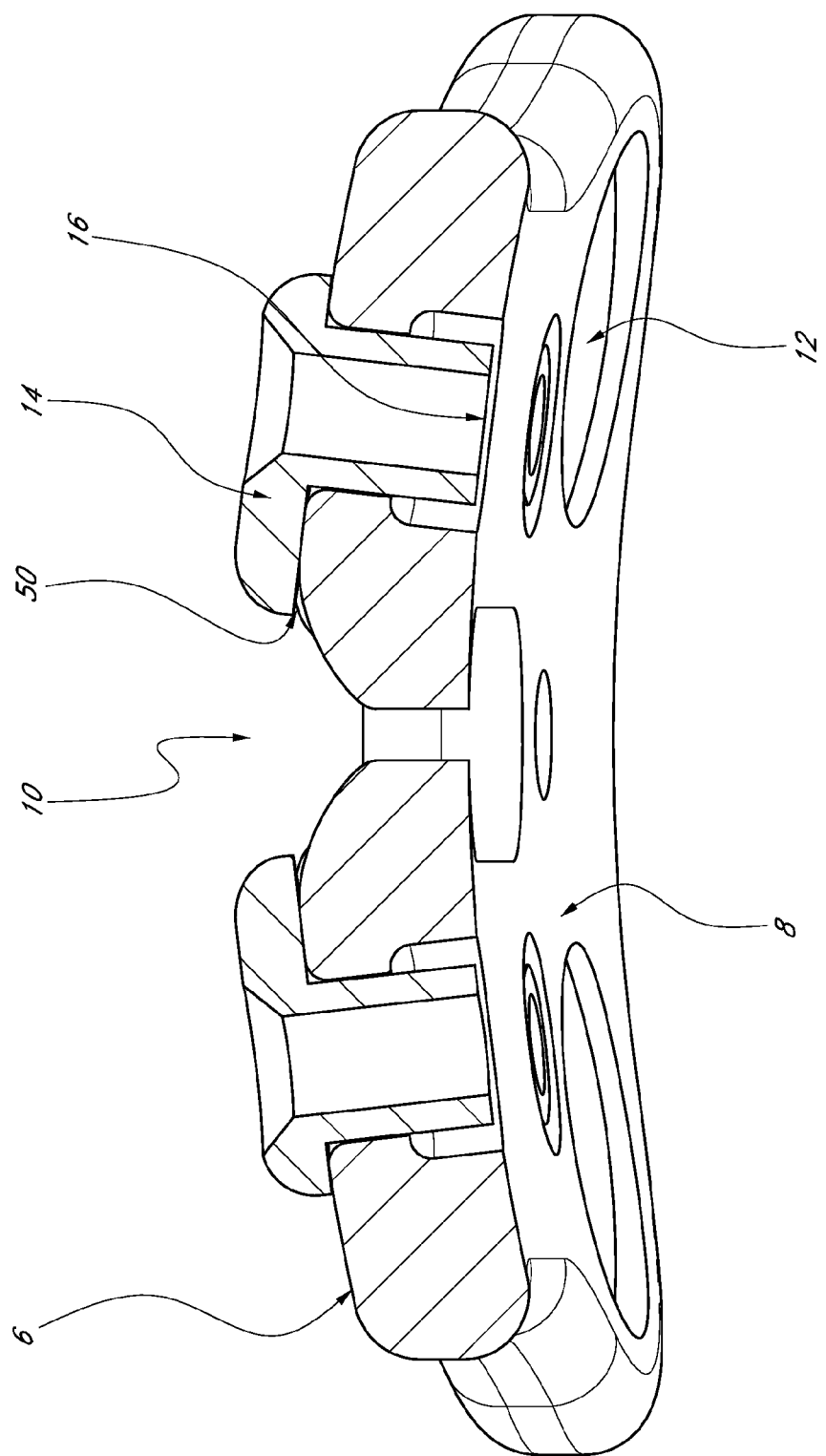
FIG. 8 is a cross-sectional view of the plate and blocking elements illustrated in FIG. 1.

FIG. 8 illustrates a cross-sectional view of one embodiment of plate 10 with blocking element 14 coupled to plate 10 by rivet 16. Contact surface 50 provides a frictional force upon rotation of blocking element 14 which aids in stopping blocking element 14 in a blocked position to at least partially cover bone screw receiving hole 12.

Figure 13:
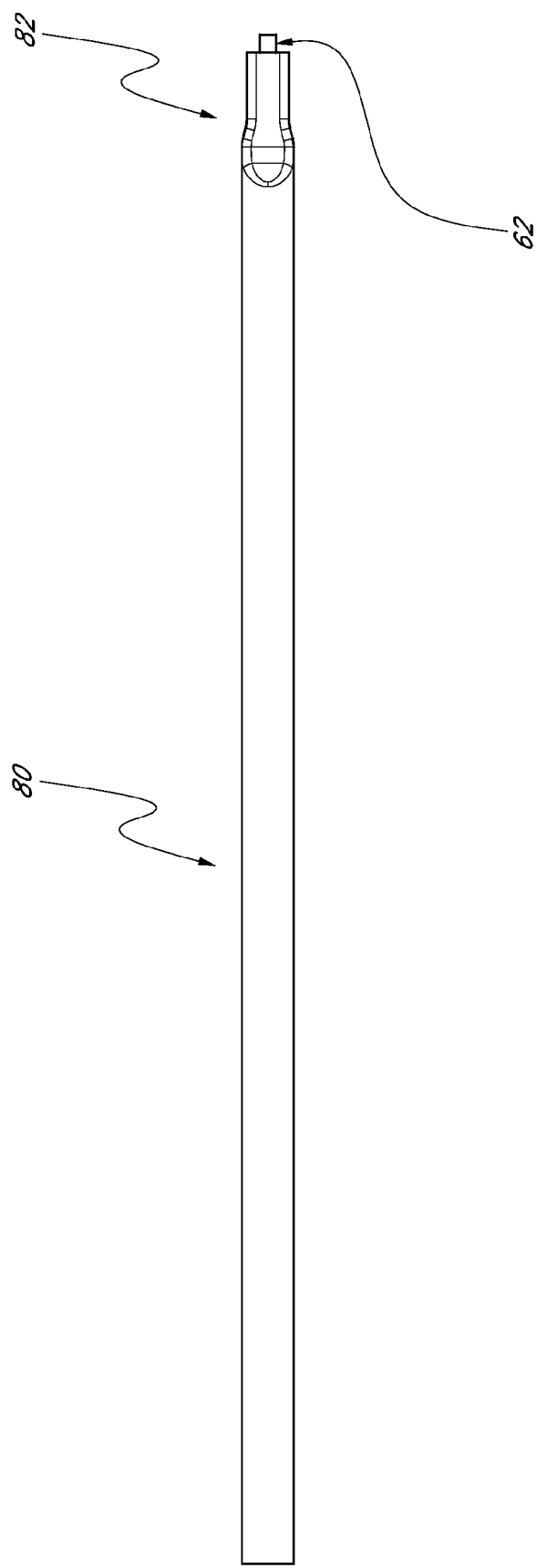
FIG. 13 is a side view of the tool illustrated in FIG. 12.

FIGS. 12 and 13 illustrate one embodiment of a tool 80 with an actuation portion 82 and a positioning tip 62. The actuation portion 82 is non-circular and the positioning tip 62 is cylindrical and can be used to position the tool relative to the plate via tool receiving hole 44 (as seen in FIG. 5). In yet other embodiments, the actuation portion 82 and/or positioning tip 62 may be a variety of shapes or sizes, including but not limited to rectangular, spherical, triangular, elliptical, and/or hexagonal shapes.

FIGS. 9-11 illustrate a tool 80 with an actuation portion 82 that may be used in some embodiments to simultaneously rotate multiple blocking elements 14 into a blocked position to at least partially cover bone screw receiving hole 12 as depicted, for example, in FIG. 11. In certain embodiments, tool 80 may contain an actuation portion 82 having a first cross-sectional length dimension 84 and a second cross-sectional width dimension 86. First length dimension 84 may be greater than second width dimension 86. The smaller width dimension 86 may be less than or equal to the distance between each of the tool contacting surfaces 42 of two blocking elements 14. Thus, upon rotation of tool 80 and actuation portion 82, greater length dimension 84 provides a larger space between the tool contacting surfaces 42 thus rotating blocking elements 14 and blocking surfaces 40 into blocked positions to at least partially cover bone screw receiving hole 12 (as seen in FIG. 11).

In certain embodiments, blocking element 14 is rotated into the blocked position without contacting the enlarged head 28 of bone screw 20. Upon attachment to a patient's vertebra, the enlarged head 28 of the bone screw 20 is tightened to recess beneath the upper surface 6 of the plate into the bone screw receiving hole 12. Blocking element 14 thus limits backout of the bone screw 20 beyond the upper surface 6 of the plate 10. The initial space between enlarged head 28 and blocking element 14 upon rotation of blocking element 14 allows for flexibility for the surgeon in selection of bone screw length and the amount of rotation of said bone screw. In addition, this initial space allows for the bone screw 20 to more comfortably settle into place post surgery. In some other embodiments, blocking element 14 at least partially contacts at least a portion of the bone screw 20, thereby blocking and locking the bone screw in place.

Figure 14:
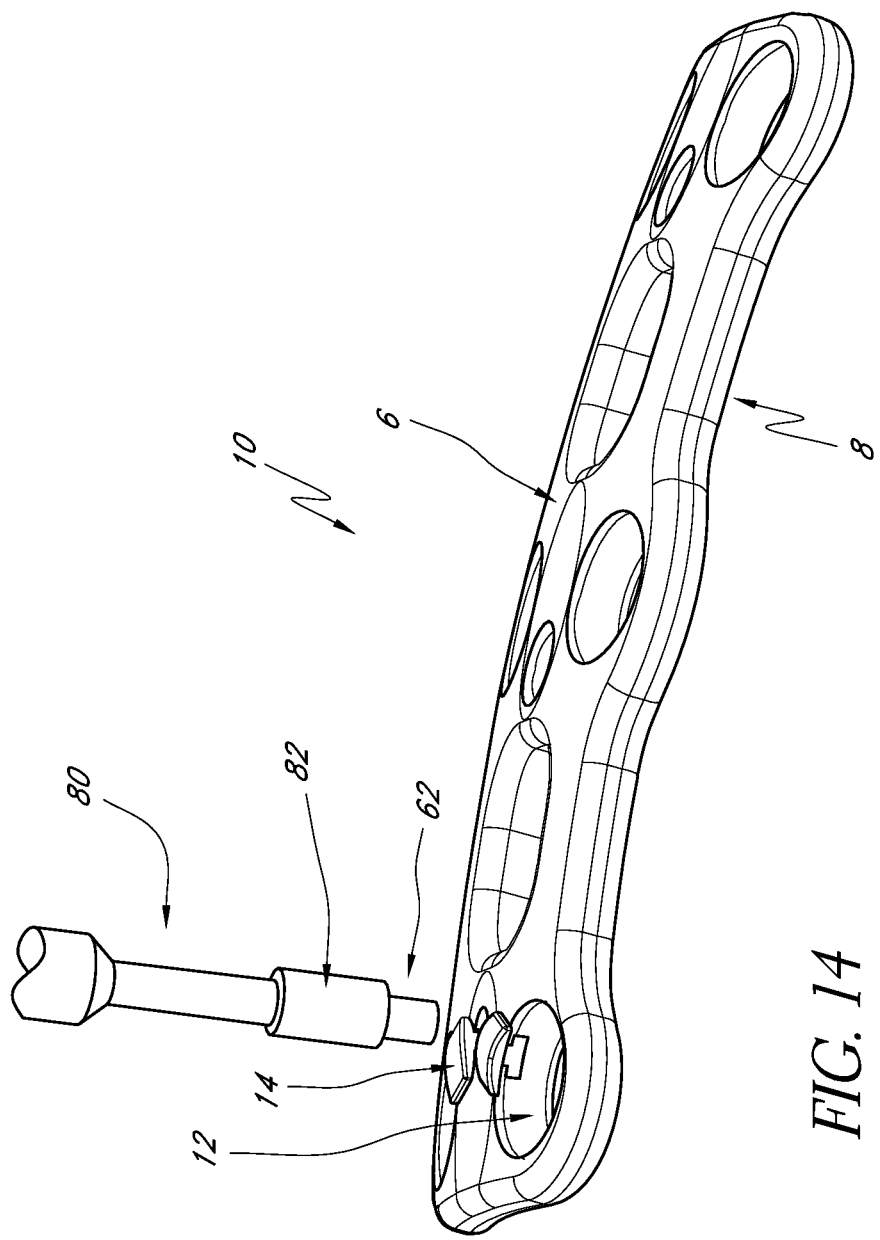
FIG. 14 is a perspective view of one embodiment of a plate, a tool, and blocking elements of a bone plate system.
Figure 15:
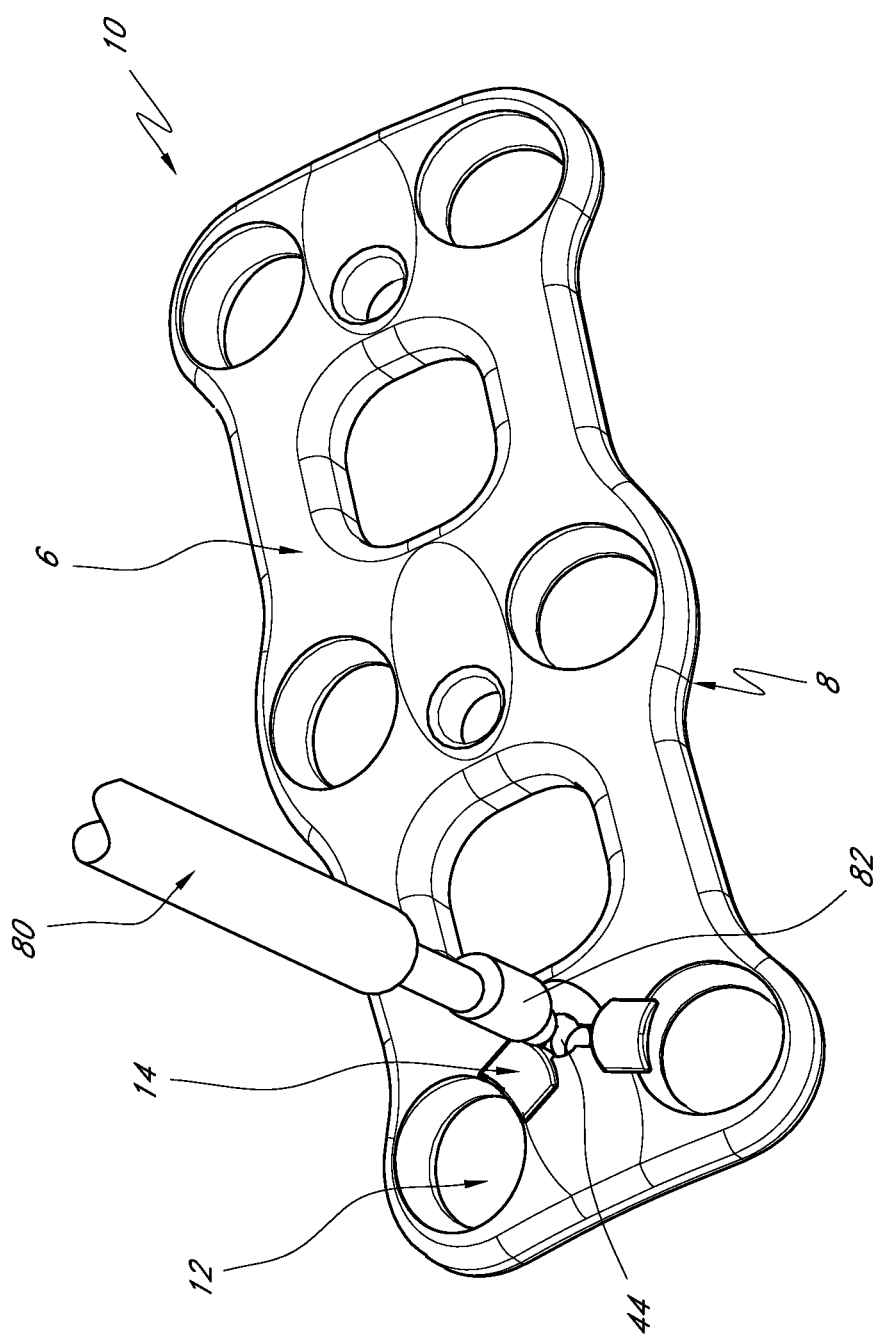
FIG. 15 is a top perspective view of the plate illustrated in FIG. 14.

FIGS. 14-15 illustrate another embodiment where blocking element 14 slides into the blocked position without contacting the enlarged head 28 of bone screw 20. Tool 80 with an actuation portion 82 may be used in some embodiments to slide one or more blocking elements 14 into a blocked position to at least partially cover bone screw receiving hole 12. For example, tool 80 may contain a rounded actuation portion 82 and a positioning tip 62 configured to connect to plate 10 via tool receiving hole 44. After connecting tool 80 to plate 10, tool 80 may be rotated to allow actuation portion 82 to contact blocking elements 14 and slide them over bone screw receiving holes 12. Blocking elements 14 may be held in a second blocked position through a surface frictional force. Upon attachment to a patient's vertebra, the enlarged head 28 of the bone screw 20 is tightened to recess beneath the upper surface 6 of the plate into the bone screw receiving hole 12. Blocking element 14 thus limits backout of the bone screw 20 beyond the upper surface 6 of the plate 10. The initial space between enlarged head 28 and blocking element 14 upon rotation of blocking element 14 allows bone screw 20 to comfortably settle into place post surgery.

FIGS. 16A-16C illustrate another embodiment where blocking element 14 slides and contacts at least a portion of the bone screw 20, thereby blocking and holding the bone screw in place. Blocking element 14 may engage the bone screw 20 in a variety of ways. For example, blocking element 14 may slide into a blocked position and engage the bone screw shaft just beneath the enlarged head 28 of the bone screw 20. Further, as depicted in FIG. 16C, blocking element 14 may slide into a blocked position by engaging the bone screw head and bone screw shaft simultaneously. As depicted in FIG. 16B, blocking element 14 may be completely recessed within plate 10 under the upper surface 6. The recessed blocked element may be moved to a second blocked position to engage bone screw 20 by a tool through tool receiving hole 44.

Figure 17:
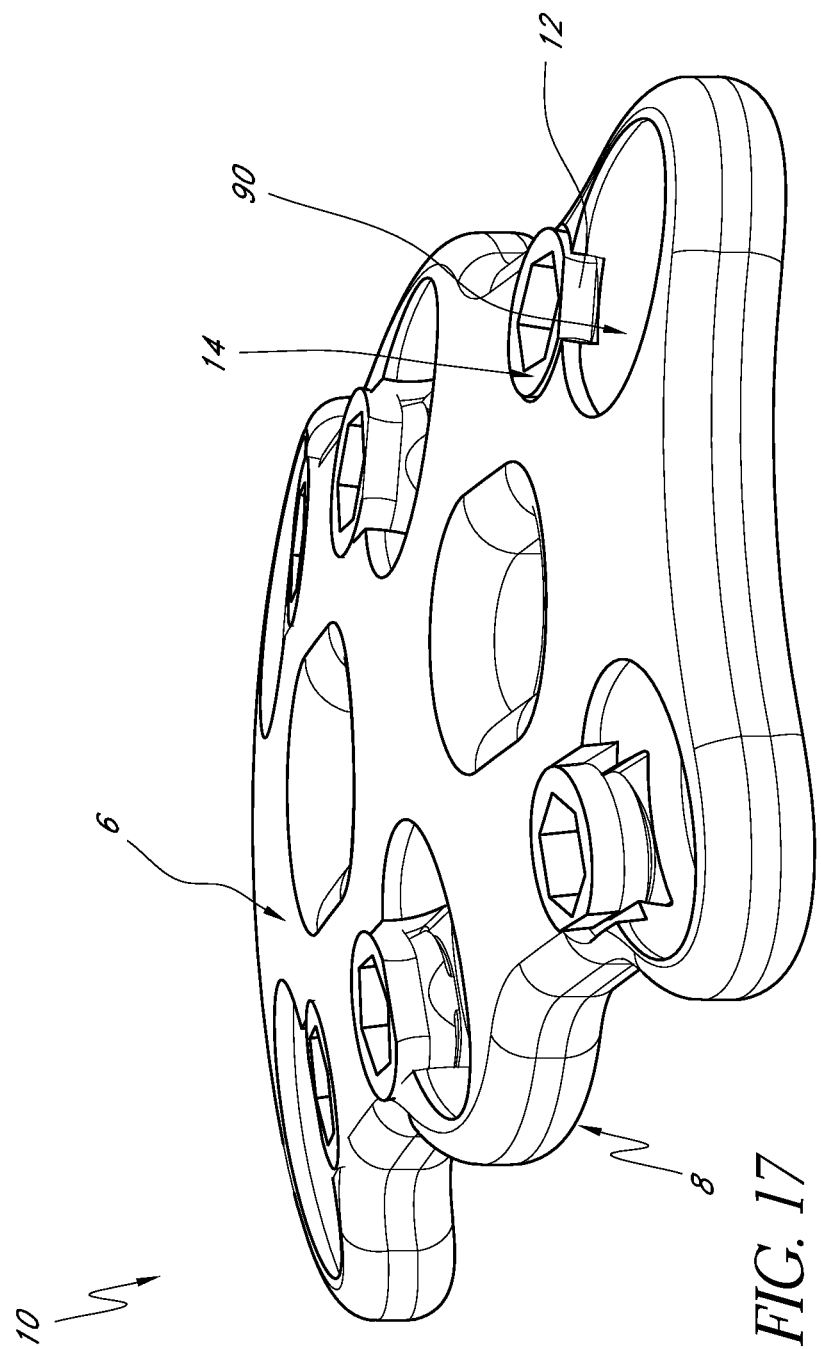
FIG. 17 is a perspective view of one embodiment of blocking elements and a plate of a bone plate system.
Figure 18:
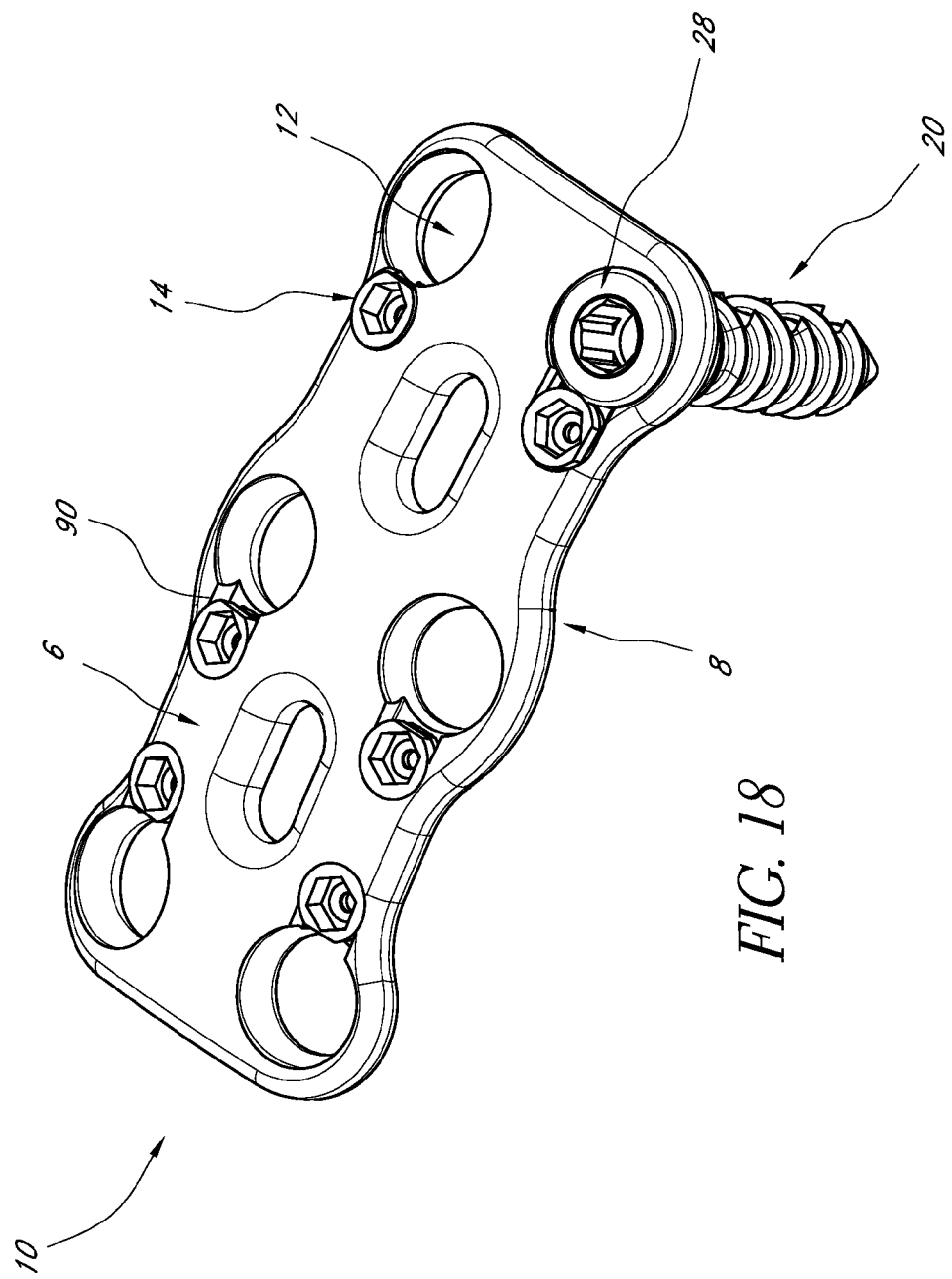
FIG. 18 is a perspective view of the bone plate system illustrated in FIG. 17.

FIGS. 17-18 illustrate another embodiment where blocking element 14 is recessed into the plate adjacent to bone screw 20. Blocking element 14 may rotate into the blocked position by contacting the side of enlarged head 28 of bone screw 20. Blocking element 14 may be held in a second blocked position by a surface frictional force with the side of the enlarged head 28 of bone screw 20. In some embodiments, blocking element 14 is circular with one cutout 90 that faces bone screw 20 upon insertion. In an initial unblocked position, the cutout 90 is designed to limit contact with bone screw 20. Upon rotation, the rounded portion of blocking element 14 contacts bone screw 20, thus holding the bone screw in place. Bone screw 20 may contain slots to mate with protrusions on blocking element 14. Upon rotation of blocking elements 14, the protrusions connect with the slots on bone screws 20 to more effectively limit backout. Cutout 90 may be shaped to contact the recess wall of the housing of blocking element 14 upon rotation, thus more effectively holding blocking element 14 in a second blocked position via a surface frictional force.

Figure 19:
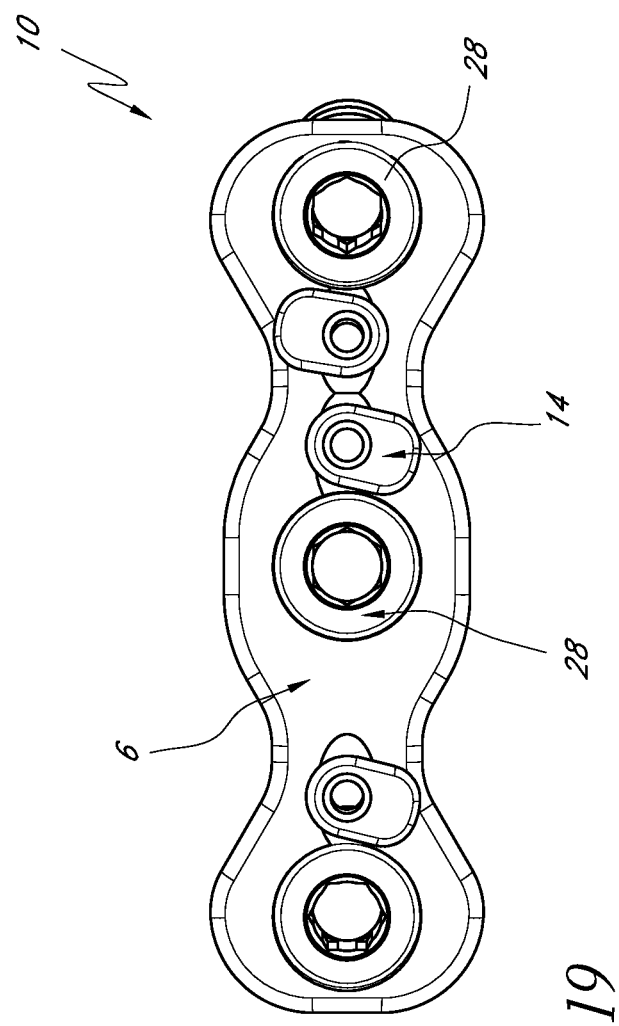
FIG. 19 is a top view of one embodiment of blocking elements, bones screws, and a plate of a bone plate system.
Figure 20:
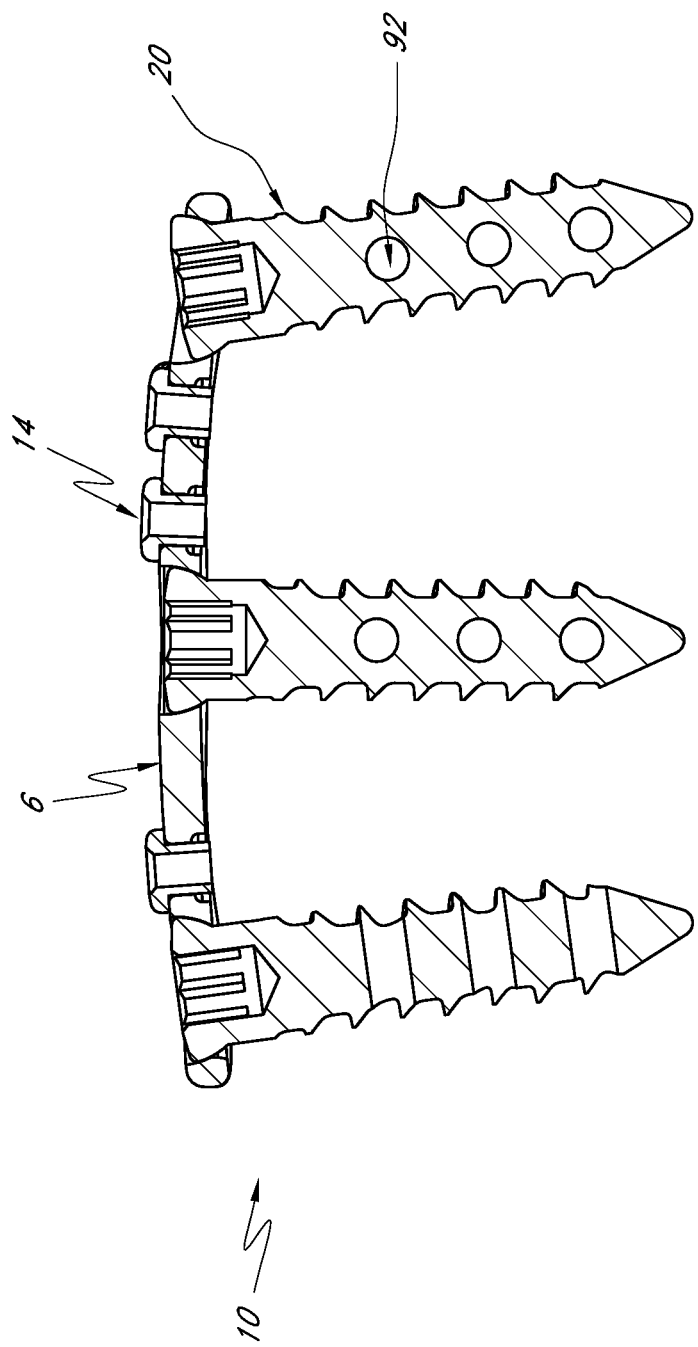
FIG. 20 is a cross-sectional view of the plate illustrated in FIG. 19

FIGS. 19-20 illustrate another embodiment where blocking elements 14 are rotated into the blocked position without contacting the enlarged heads 28 of exactly three bone screws 20 along a single axis. Blocking elements 14 may be riveted to plate 10 on upper surface 6. Further, bone screws 20 may contain bone screw holes 92 that promote bone growth into bone screws 20 after attachment to the vertebra. In other embodiments, screws comprising bone screw holes 92 may similarly be used in combination with other plate and blocking element embodiments disclosed herein. In some other embodiments more or less bone screws could be similarly arranged and blocked along a single axis. For example, plate 10 may contain exactly two bone screws 20, two blocking elements 14, and two bone screw receiving holes 12 with each bone screw 20 being positioned on opposing ends of plate 10. This embodiment discloses various potential advantages, including faster surgery, smaller and easier to maneuver bone plates, and the option to use larger diameter bone screws 20. A thinner width and slimmer profile allow for accurate placement of the plate on the vertebrae. In addition, smaller incisions may be required during surgery which may lead to quicker healing times and less scarring.

The embodiments shown in FIGS. 21-31 are described to contain blocking elements 14 that advantageously block more than one corresponding bone screw receiving hole 12. As discussed above, however, in other configurations the blocking elements 14 shown in these embodiments, or modifications thereof, can be arranged to block exactly one bone screw receiving hole 12. Accordingly, such alternative embodiments are envisioned and within the scope of this application.

Figure 21:
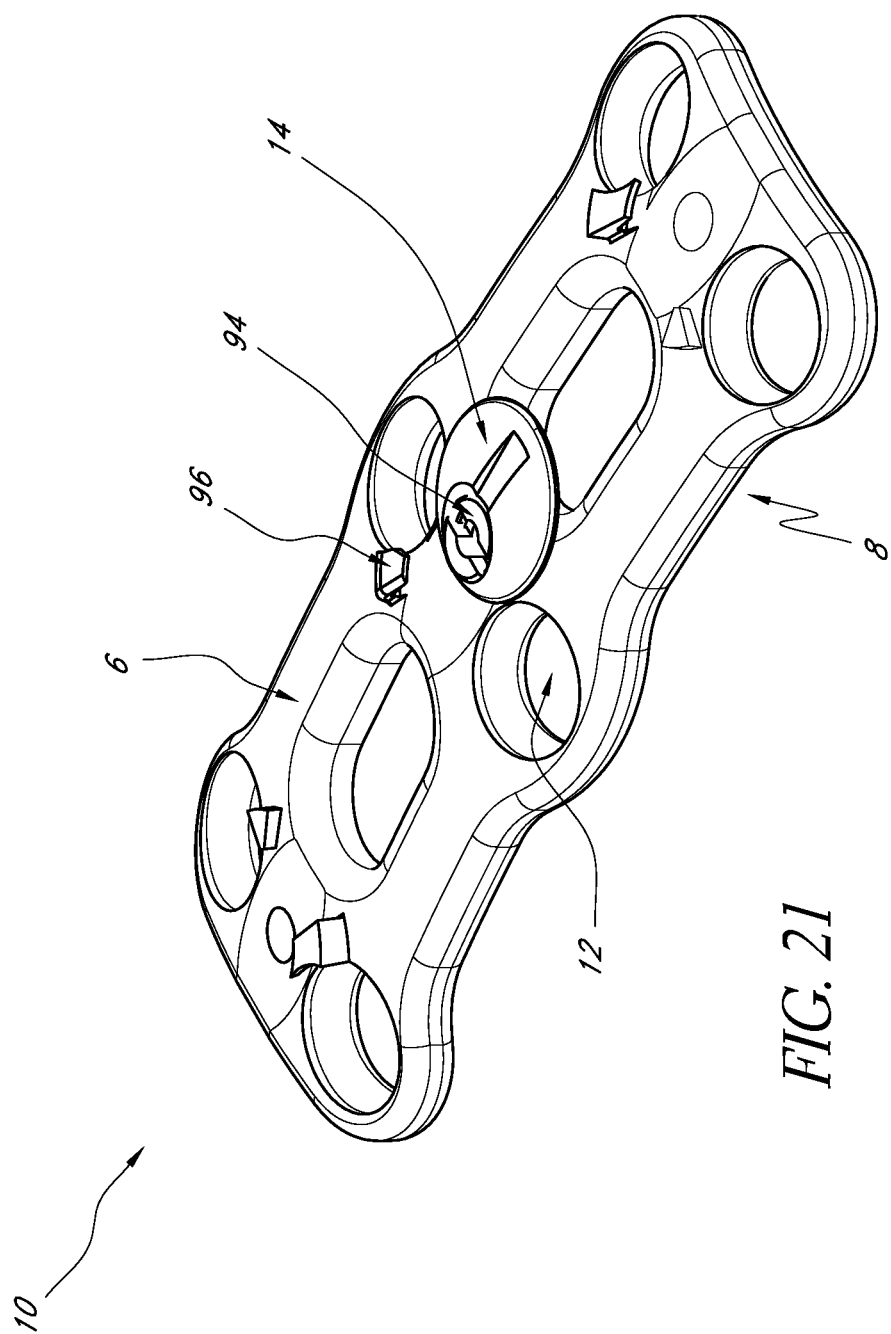
FIG. 21 is a perspective view of one embodiment of a blocking element and a plate of a bone plate system.
Figure 22:
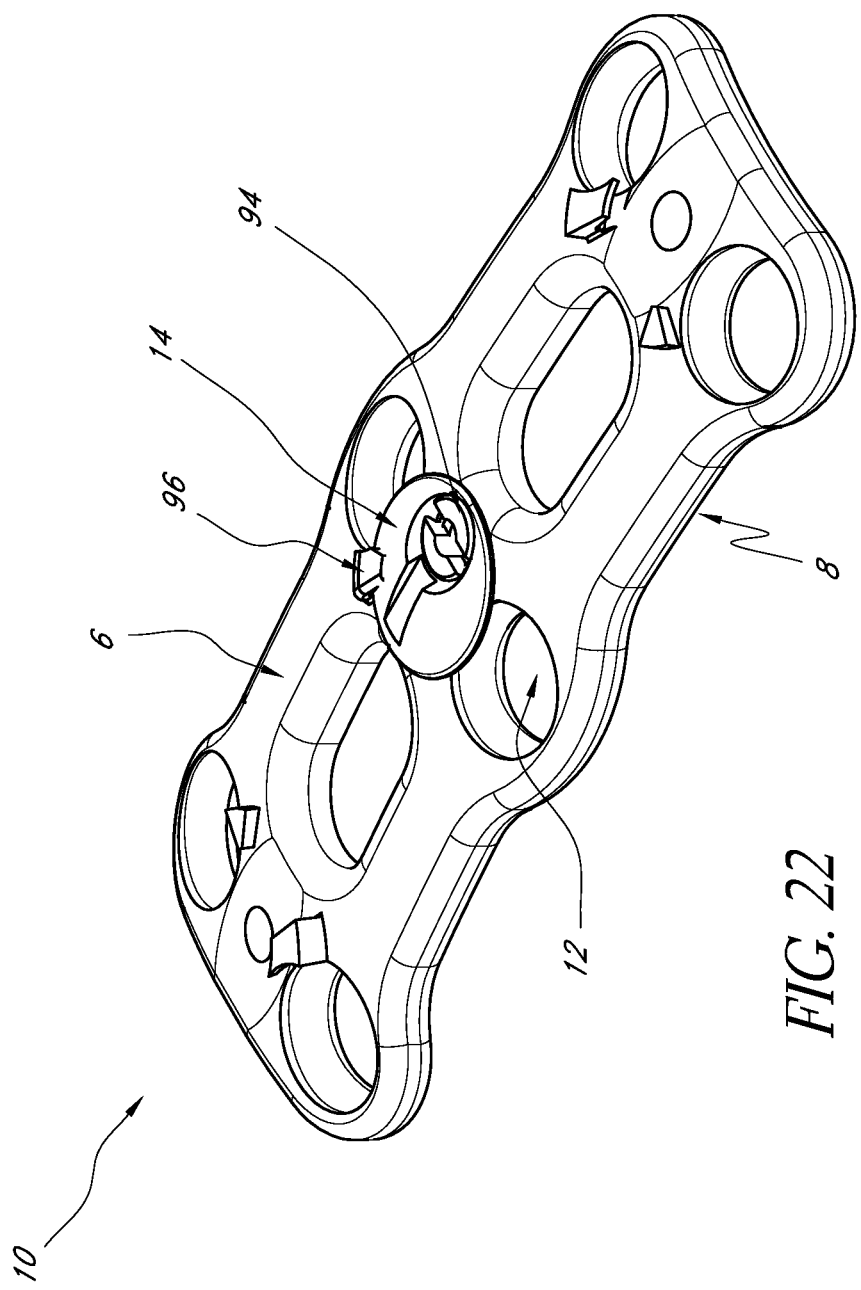
FIG. 22 is a perspective view of one embodiment of the bone plate system illustrated in FIG. 21.

FIGS. 21-24 illustrate some embodiments where offset blocking elements 14 are rotated into the blocked position without contacting the enlarged heads 28 of two bone screws 20. As depicted in FIG. 21-22, blocking element 14 may be a washer that is connected to plate 10 via a set screw offset from the center of the blocking element 14. The offset set screw 94 allows for blocking element 14 to sit further away from the bone screw receiving holes 12 in an initial unblocked position. Blocking elements 14 may be pivoted around the offset set screw 94 into a final blocked position to at least partially cover two bone screw receiving holes 12 to limit backout of the bone screws 20 beyond the upper surface 6 of the plate 10. The offset design allows a surgeon additional space to work with the enlarged heads 28 of bone screws 20 prior to moving blocking elements 14 to a blocked position. Blocking elements 14 may also be non-circular. Plate 10 may contain a stopper 96 on the upper surface 6 that limits rotation of blocking element 14 beyond the blocked position. The stopper 96 may also assist in securing blocking element 14 in a blocked position.

Figure 23:
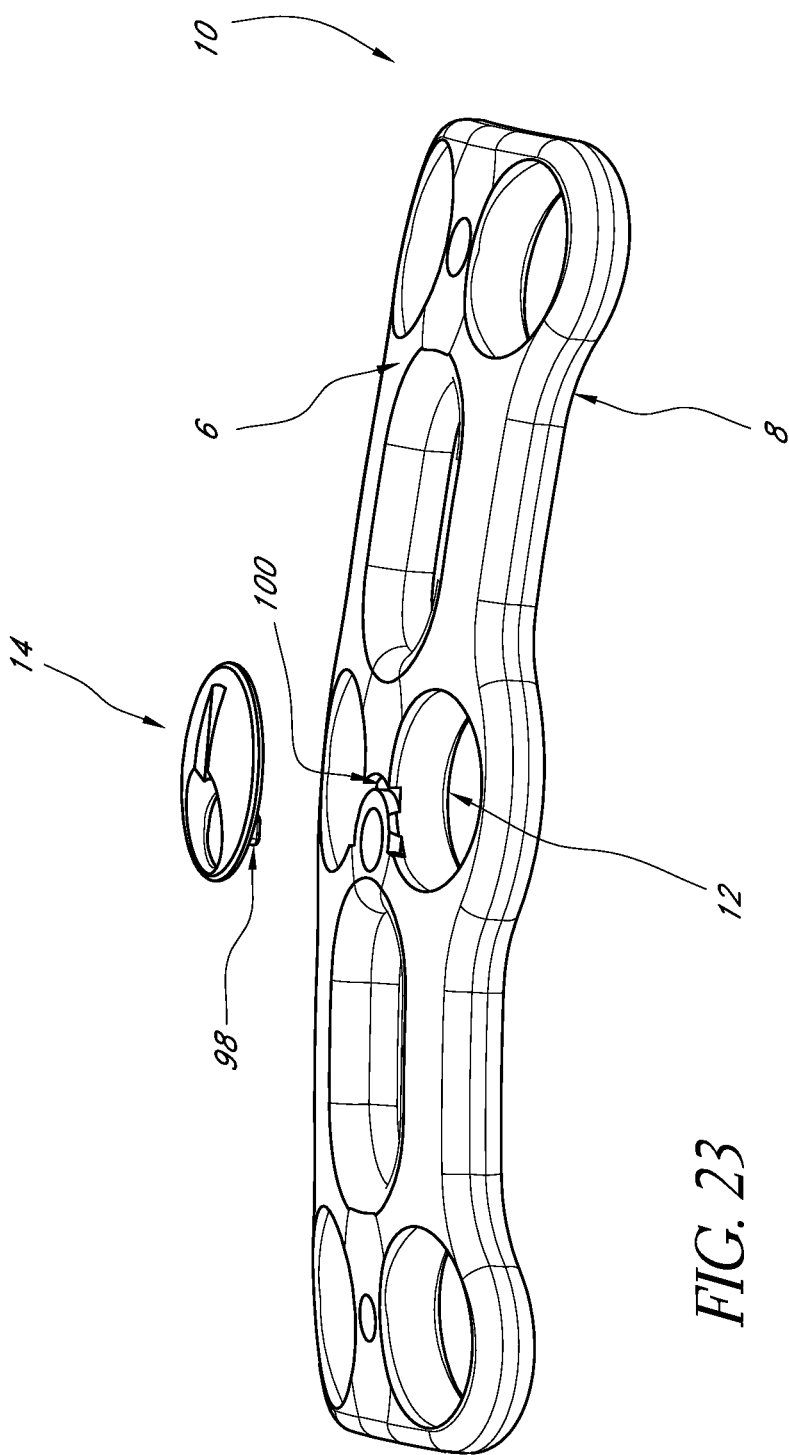
FIG. 23 is a perspective view of one embodiment of a blocking element and a plate of a bone plate system.
Figure 24:
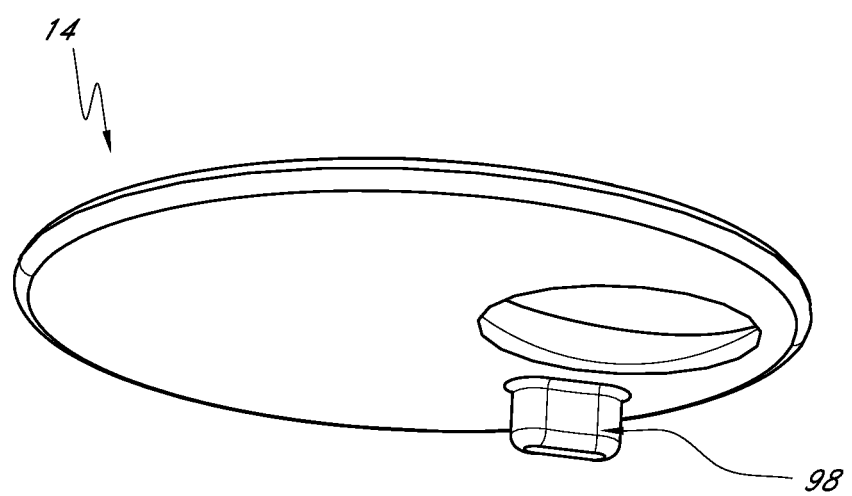
FIG. 24 is a bottom perspective view of the blocking element of the plate illustrated in FIG. 23.

FIGS. 23-24 illustrate one embodiment with a studded washer, as a blocking element 14, and a corresponding groove 100 on plate 10. In one embodiment, the groove 100 is C-shaped groove and allows the stud 98 to provide rotational tracking of blocking element 14 as it moves between blocked and unblocked positions. In addition, blocking element 14 may be attached to the plate with an offset set screw 94. The stud 98 may be placed on embodiments with non-circular blocking elements. The groove 100 may take on a variety of circular and non-circular shapes including but not limited to elliptical, circular, L-shapes, and V-shapes.

Figures 25A, 25B:
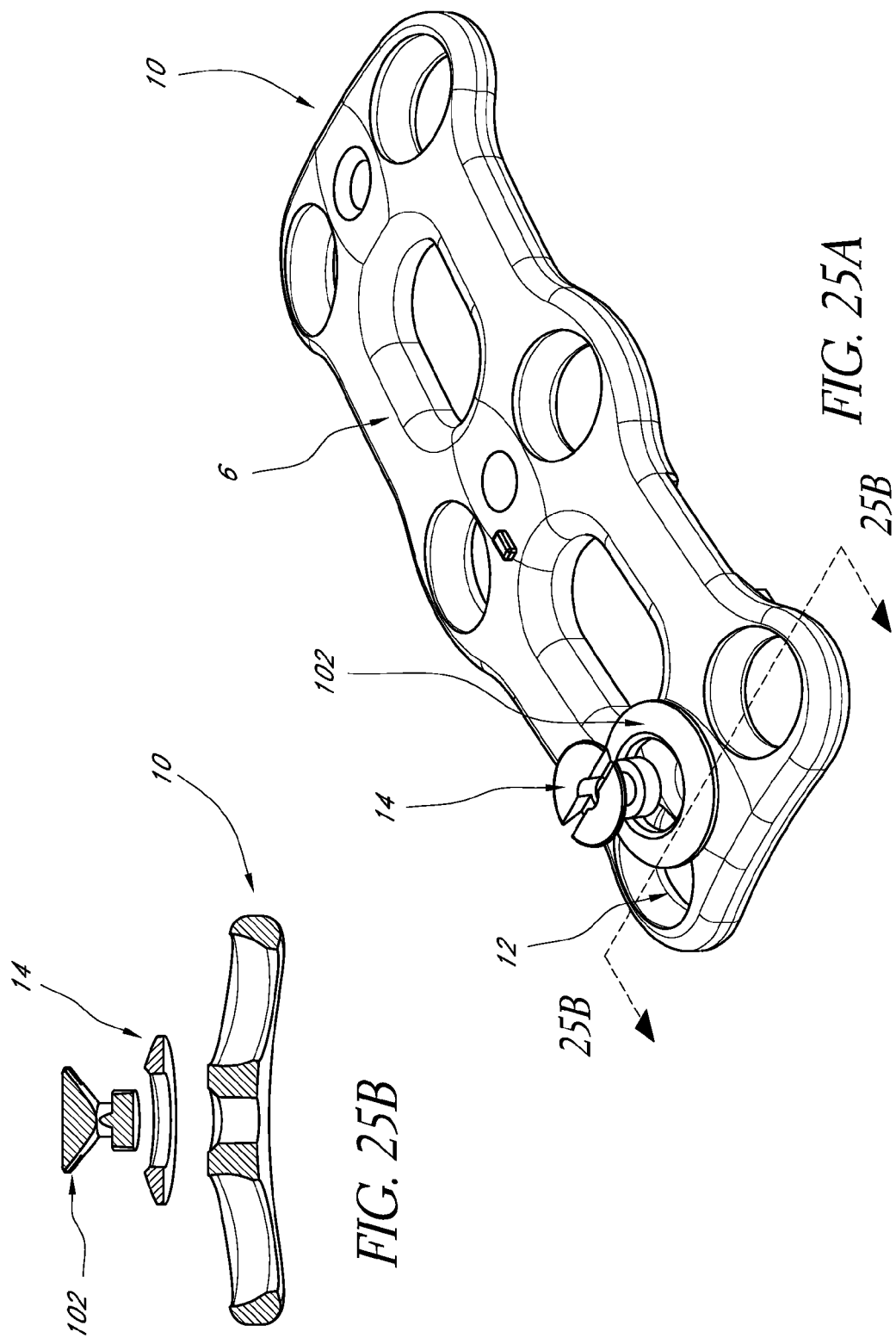
FIG. 25A is a perspective view of one embodiment of a blocking element, central set screw, and a plate of a bone plate system.
FIG. 25B is a cross-sectional view of the plate illustrated in FIG. 25A.

FIGS. 25-28 illustrate some embodiments where blocking elements 14 are secured into blocked position by tightening a set screw 102 in the center of said blocking elements 14. As depicted in FIGS. 25-26, in their blocked positions, bone screws 20 do not contact the enlarged heads 28 of at least two bone screws 20. For example, blocking element 14 may be ring-shaped and adapted to mate with the set screw head. Blocking element 14 is adjustable as it may move relative to plate 10 and into an unblocked position covering no bone screw receiving holes 12 when the set screw 102 has not been tightened into plate 10.

Additionally, in an initial unfixed position, blocking element 14 is adjustable to cover one bone screw receiving hole 12 while moving away from a neighboring bone screw receiving hole 12. Hence, when the set screw 102 is tightened into the plate 10 and mates with blocking element 14, blocking element 14 returns to being centered by set screw 102 and is fixed in a blocked position covering at least a portion of one bone screw receiving hole 12. In yet other embodiments, the set screw 102 may be offset from the center of blocking element 14 (as seen in FIG. 21).

Figure 27:
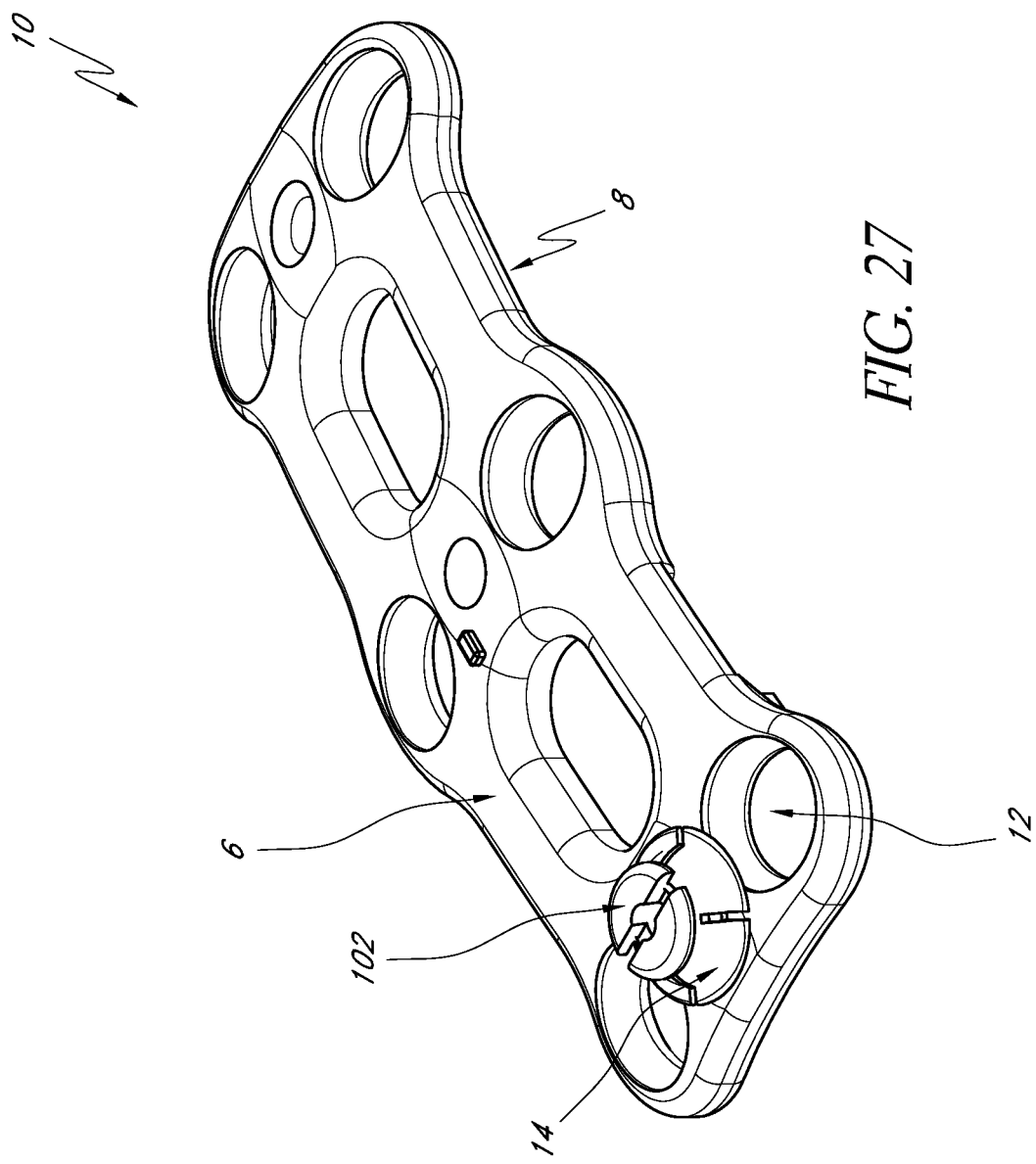
FIG. 27 is a perspective view of one embodiment of a blocking element, central set screw, and a plate of a bone plate system.
Figure 28:
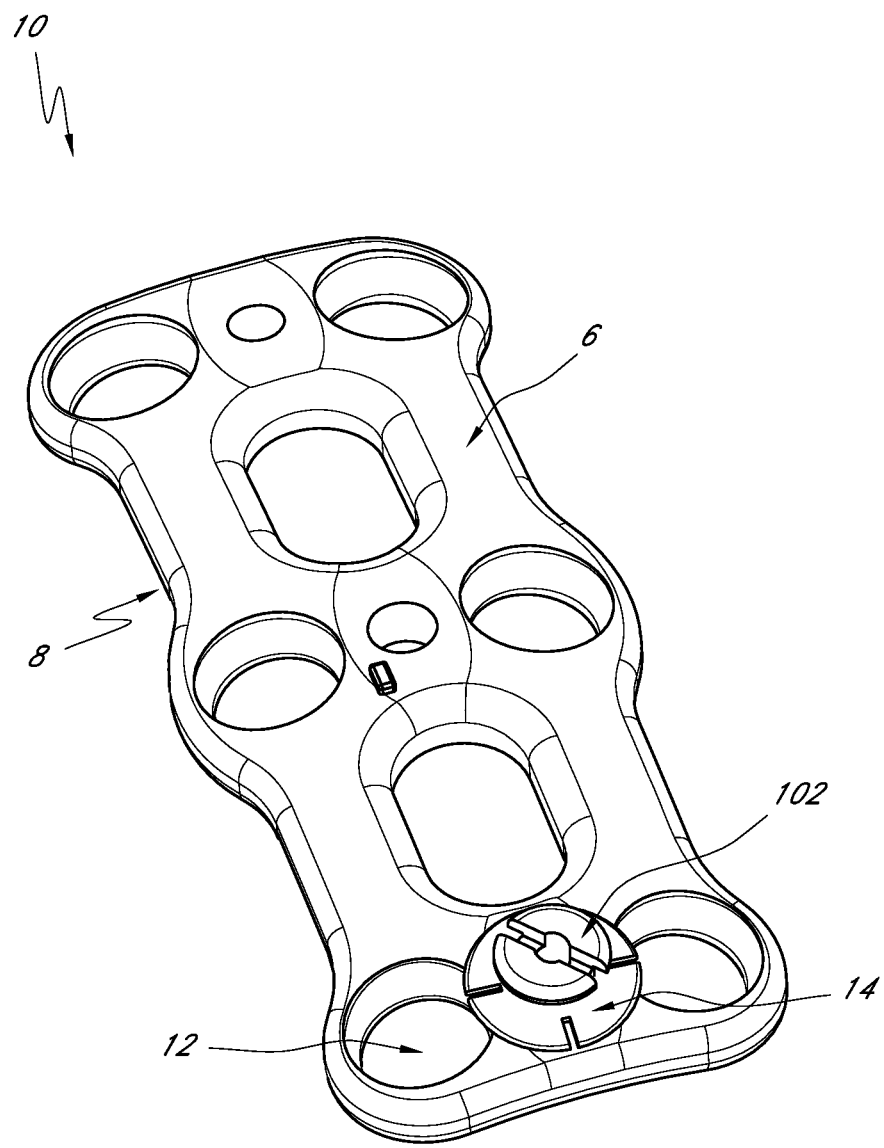
FIG. 28 is a top perspective view of the plate illustrated in FIG. 27.

In yet another embodiment, as depicted in FIGS. 27-28, blocking element 14 may be connected to set screw 102 and expanded into a blocked position by depressing set screw 102. Blocking element 14 is adjustable in shape. For example, as depicted in FIG. 27, blocking element 14 may be plastic and hemispheric in an initial unblocked position. Other suitable materials and shapes can also be used. After insertion of bone screws 20, set screw 102 may be tightened to depress the hemisphere-shaped blocking element 14 into a flat element with an increased diameter. The increased diameter of the depressed blocking element 14 at least partially covers at least two bone screw receiving holes 12 to limit backout of bone screws 20 beyond the upper surface 6 of the plate 10. These embodiments allow a surgeon to quickly complete a surgical procedure by easily securing blocking elements 14 into blocked positions, because set screws 102 and blocking elements 14 can be pre-attached to plate 10 for convenience and simply tightened without maneuvering blocking elements 14.

Figure 29:
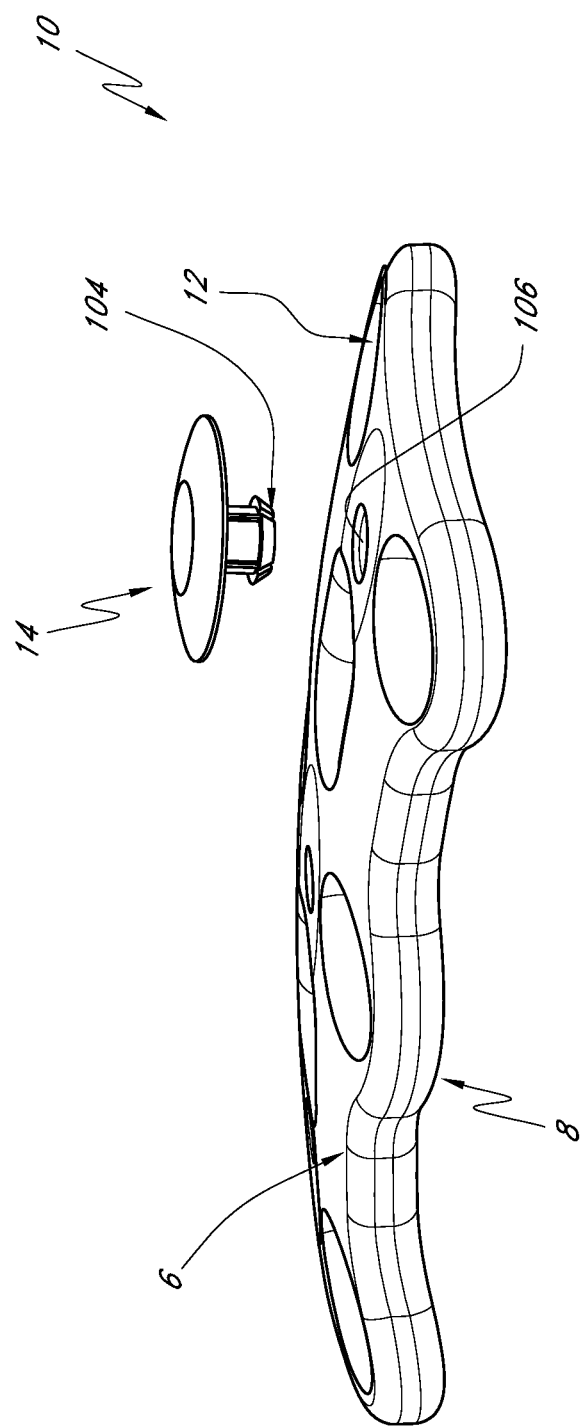
FIG. 29 is a perspective view of one embodiment of a blocking element and a plate of a bone plate system.
Figure 30:
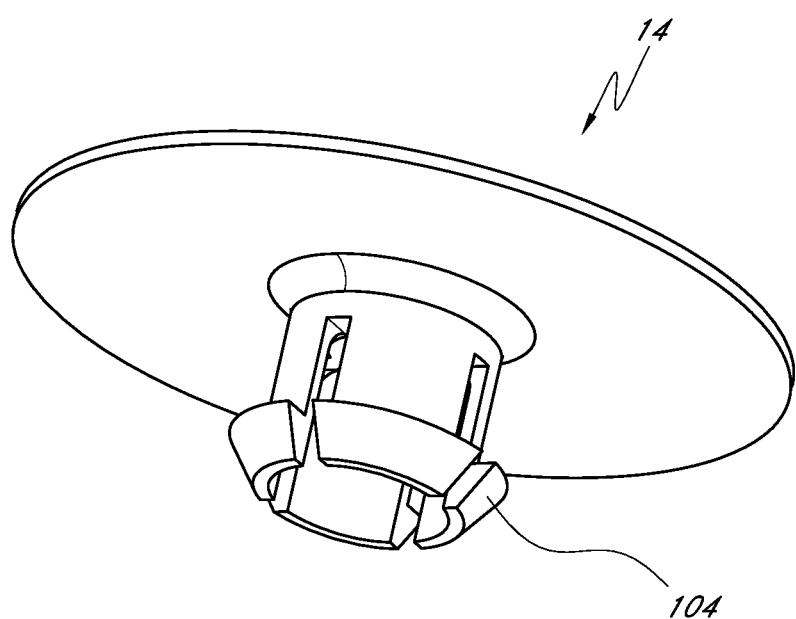
FIG. 30 is a bottom perspective view of the blocking element of the plate illustrated in FIG. 29.

FIGS. 29-30 illustrate some embodiments where blocking element 14 is depressed into blocked position without contacting the enlarged heads 28 of two bone screws 20. For example, blocking element 14 may be detached prior to the insertion of the bone screws 20. After insertion of the bone screws 20, blocking element 14 may be placed into a blocking element receiving hole on the upper surface 6. Upon depression of blocking element 14 into the plate 10, blocking element 14 is fixed into a blocked position. Bendable lip projections 104 contact the lower surface 8 or an intermediate surface and the blocking element head contacts the upper surface 6 of plate 10. For example, bendable lip projections 104 may contract while moving through the blocking element receiving hole 106 as blocking element 14 is depressed into plate 10. When the bendable lip projections 104 move beyond the lower surface 8 or intermediate surface of plate 10, they expand beyond the diameter of the blocking element receiving hole 106. Hence, the bendable lip projections 104 secure blocking element 14 by contacting the lower surface 8 of plate 10.

Figure 31:
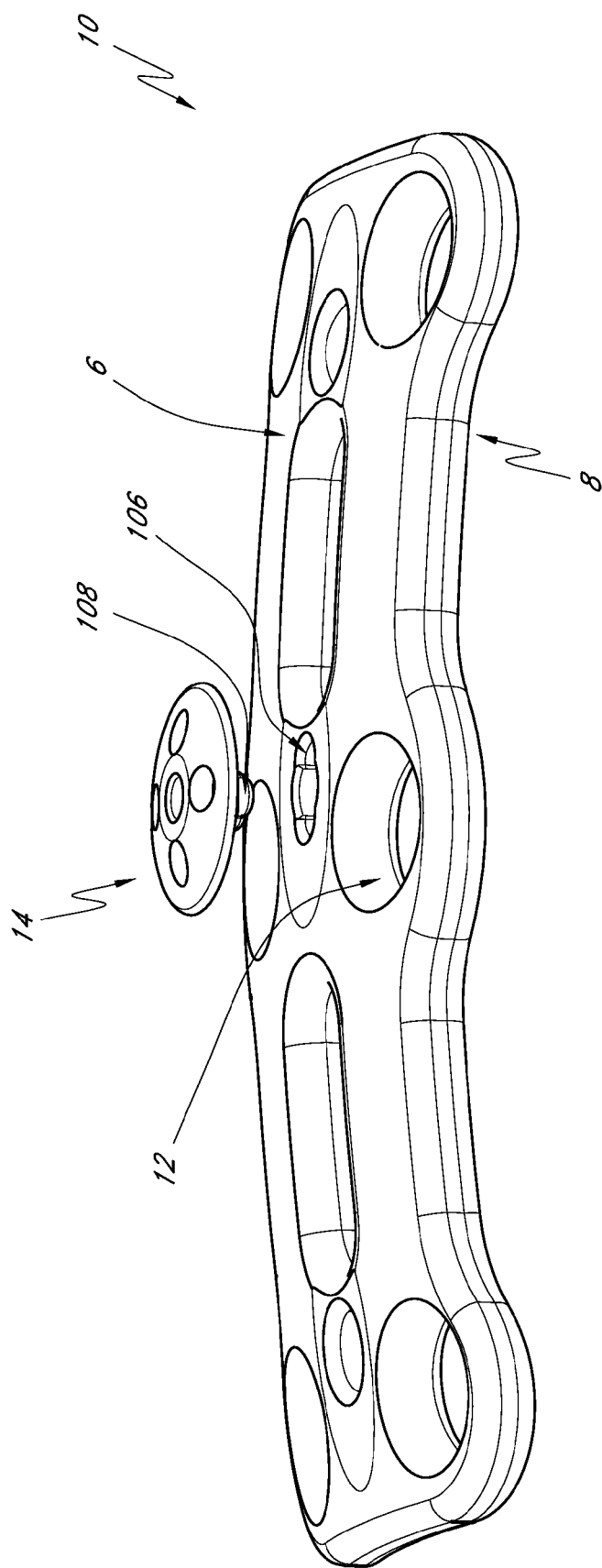
FIG. 31 is a side perspective view of one embodiment of a blocking element and a plate of a bone plate system.

FIG. 31 illustrates one embodiment where blocking element 14 may be depressed and subsequently rotated into blocked position without contacting the enlarged heads 28 of two bone screws 20. For example, blocking element 14 may have a non-circular shaft and plate 10 may contain a corresponding non-circular blocking element receiving hole 106. For example, blocking element shaft has lip projections 108. After blocking element 14 is depressed to the point where the lip projections 108 extend beyond the lower surface 8 or intermediate surface of plate 10, blocking element 14 is rotated so the lip projections 108 contact the lower surface 8 or intermediate surface and fix blocking element 14 in place. Thus, upon rotation of blocking element 14, two bone screw receiving holes 12 are at least partially covered to limit backout of the bone screws 20 beyond the upper surface 6 of the plate 10. This embodiment provides an efficient blocking element 14 that simplifies the blocking element mechanism for surgical implantation. The entire blocking mechanism is built into blocking element 14, which only needs to be depressed and rotated after a surgeon has inserted bone screws 20. The strength of blocking element 14 does not depend on a separate attachment mechanism to fix blocking element 14 to plate 10. Rather, the strength of blocking element 14 may be intensified by using the upper and lower surfaces of plate 10 to contact the sturdy, potentially titanium, blocking element 14. Other materials can also be used.

In some embodiments, individual blocking elements 14 can be rotated into a final blocking position independently of other blocking elements 14 with or without the use of a tool. This provides additional flexibility for the surgeon in either utilizing fewer bone screws 20 or choosing to block or unblock only one bone screw receiving hole 12 at a time. For example, if two bone screw receiving holes 12 have been blocked by simultaneously rotating multiple blocking elements 14 using the tool 80 but the surgeon would like to unblock only one bone screw receiving hole 12 to adjust the corresponding individual bone screw 20, the surgeon may do so without disturbing the other blocking elements 14 or bone screws 20 already in place.

A number of surgical methods can be used to implant bone plate systems. For example, several surgical methods are described in U.S. Pat. No. 7,674,279, which is hereby incorporated by reference herein in its entirety. For example, the patient can be placed on the operating room table in the supine position with the head in slight extension and slight rotation opposite the side of incision.

After decompression and interbody grafting procedures have been completed, anterior osteophytes can be removed to provide a contoured contact surface for positioning the plate 10. The plate 10 can be selected so that the edges do not extend over adjacent disc spaces. The plate 10 can be pre-contoured with lordotic curvature to minimize the amount of intra-operative contouring required. A plate bender can also used for contouring.

The plate 10 can then be positioned over vertebral bodies using a plate holder, and then the plate 10 can be confirmed that it is properly aligned in mediolateral and caudocranial position. The position of the plate 10 can be temporary fixed using pins (e.g. temporary pins, etc.). The pins can be inserted with a tool (e.g. screwdriver, etc.). The pins can be inserted through any of the screw holes and can provide stability during placement of the bone screw 20.

An awl may be used to create a pilot hole before inserting the bone screw 20. The awl is placed in one of the bone screw receiving holes 12 of the plate 10. In certain embodiments, the awl is placed at an angle of up to about 14° from a perpendicular axis to the plate 10. The awl is pressed and rotated in the bone until a depth has been reached. For example, the awl can be inserted until it has bottomed out. In certain embodiments, the awl can provide a depth of about 10 mm. Alternatively, a drill guide and drill can be used to create a pilot hole. The drill guide can be attached to the plate 10 and the drill can create a pilot hole. In certain embodiments, the drills are about 12, 14, or 16 mm in length. The bone screws 20 can be self-tapping and/or self-drilling screws so that tapping may not be used. In some cases, where the bone is hard cortical bone, tapping may still be used. In certain embodiments, the tap is provided at a depth of about 10 mm. In certain embodiments, the self-tapping or self-drilling screws have a length of about 12, 14, 16, or 18 mm with a diameter of about 4.0 mm. An about 4.5 mm diameter screw can also be used if there is additional bone purchase. The above screw lengths are measured from under the head 28 of the bone screw 20 to the end of the distal end 22 of the screw 20. In certain embodiments, the screws are inserted using a hex screwdriver.

The plate 10 may vary in size. For example, the length and level number of the plate 10 may vary. The level number of the plate 10 indicates the number of vertebral body connections made by plate 10. In some embodiments, a 1-level plate 10 preferably has a length from about 20 mm to about 32 mm and connects two vertebral bodies. In some embodiments, a 2-level plate 10 preferably has a length from about 37 mm to about 55 mm and connects three vertebral bodies. In some embodiments, a 3-level plate 10 preferably has a length from about 54 mm to about 75 mm and connects four vertebral bodies. In some embodiments, a 4-level plate preferably has a length from about 69 mm to about 89 mm and connects five vertebral bodies.

The bone screw 20 can be inserted into vertebrae until it rests firmly inside the bone receiving hole 12 of the plate 10. Once the bone screws 20 have been seated, positioned and tightened, then blocking elements 14 can be rotated to a final blocked position. If desired, the bone screws 20 can be subsequently removed by rotating blocking elements 14 to their initial unblocked position and removing the bone screws 20. In certain embodiments, the bone screws 20 can be repositioned, tightened and then blocked again without weakening in the blocking system. Visual and radiographic confirmation of plate, screw and bone graft placement can be done, and the incision can then be closed.

The various screws and methods described above provide a number of ways to carry out some preferred embodiments of the invention. Of course, it is to be understood that not necessarily all objectives or advantages described may be achieved in accordance with any particular embodiment described herein. Thus, for example, those skilled in the art will recognize that the compositions may be made and the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Similarly, the various components, features and steps discussed above, as well as other known equivalents for each such component, feature or step, can be mixed and matched by one of ordinary skill in this art to make compounds and perform methods in accordance with principles described herein.

Although the invention has been disclosed in the context of some embodiments and examples, it will be understood by those skilled in the art that the invention extends beyond these specifically disclosed embodiments to other alternative embodiments and/or uses and obvious modifications and equivalents thereof. Accordingly, the invention is not intended to be limited by the specific disclosures of preferred embodiments herein.

What is claimed is:

1. A bone plating system comprising:
a plate comprising an upper surface, a lower surface, and at least first and second bone screw receiving holes defined in the plate and extending between the upper surface and the lower surface, wherein the first and second bone screw receiving holes are aligned along a single axis such that the plate comprises a single column of bone screw receiving holes;
at least first and second bone screws, each comprising a shaft portion configured to be anchored in bone and a head portion, the head portion of each bone screw being receivable within one of the at least first and second bone screw receiving holes such that at least part of the head portion of each of the at least first and second bone screws is configured to be recessed below the upper surface of the plate; and
at least first and second blocking elements coupled to the plate proximate the at least first and second bone screw receiving holes respectively, the blocking elements being positioned over the upper surface such that lower-most surfaces of the blocking elements are positioned above the upper most surface of the plate and such that the blocking elements are rotatable between a first unblocked position that does not cover the respective bone screws and a second blocked position that covers the respective bone screws, wherein the blocking elements are oblong in shape, and each blocking element is rotationally coupled to the plate with a rivet positioned proximate a first end of the blocking element, wherein each blocking element corresponds to exactly one bone screw receiving hole and is configured to block only one bone screw receiving hole.

2. The bone plating system of claim 1, wherein the plate comprises exactly two bone screw receiving holes, exactly two bone screws, and exactly two blocking elements.

3. The bone plating system of claim 1, wherein the plate comprises exactly three bone screw receiving holes, exactly three bone screws, and exactly three blocking elements, wherein the three bone screw receiving holes are arranged along a single axis.

4. The bone plating system of claim 1, wherein in the blocked position, the blocking elements do not contact the screw heads.

5. The bone plating system of claim 1, wherein the bone screw receiving holes and rivets are aligned on a single axis.

6. The bone plating system of claim 1, wherein in the blocked position, a second end of each blocking element opposite the first end extends over one of the bone screws.

7. The bone plating system of claim 6, wherein each blocking element is pivoted about the rivet to rotate between the first unblocked position and the second blocked position.

* * * * *